(12) United States Patent
Andres et al.

(10) Patent No.: US 8,324,383 B2
(45) Date of Patent: Dec. 4, 2012

(54) METHODS OF MAKING POLYMORPHS OF BENZOATE SALT OF 2-[[6-[(3R)- 3- AMINO-1-PIPERIDINYL]-3,4-DIHYDRO-3-METHYL-2,4-DIOXO-1(2H)-PYRIMIDINYL]METHYL]-BENZONITRILE

(75) Inventors: Mark Andres, West Lafayette, IN (US); Keith Lorimer, West Lafayette, IN (US)

(73) Assignee: Takeda Pharmaceutical Company Limited, Osaka (JP)

( * ) Notice: Subject to any disclaimer, the term of this patent is extended or adjusted under 35 U.S.C. 154(b) by 205 days.

(21) Appl. No.: 12/536,377

(22) Filed: Aug. 5, 2009

(65) Prior Publication Data

US 2009/0306379 A1    Dec. 10, 2009

Related U.S. Application Data

(63) Continuation of application No. 11/531,595, filed on Sep. 13, 2006, now abandoned.

(51) Int. Cl.
*C07D 239/22* (2006.01)
*A61P 3/10* (2006.01)
*A61P 3/04* (2006.01)

(52) U.S. Cl. .................................................. 544/312
(58) Field of Classification Search .................. 544/312
See application file for complete search history.

(56) References Cited

U.S. PATENT DOCUMENTS

| | | | |
|---|---|---|---|
| 3,322,756 A | 5/1967 | Hilmer et al. | |
| 3,544,570 A | 12/1970 | Timmler et al. | |
| 3,823,135 A | 7/1974 | Pilgram et al. | |
| 3,960,949 A | 6/1976 | Ahrens et al. | |
| 4,494,978 A | 1/1985 | Chan | |
| 4,687,777 A | 8/1987 | Meguro et al. | |
| 4,935,493 A | 6/1990 | Bachovchin et al. | |
| 5,002,953 A | 3/1991 | Hindley et al. | |
| 5,366,862 A | 11/1994 | Venton et al. | |
| 5,387,512 A | 2/1995 | Balani et al. | |
| 5,433,955 A | 7/1995 | Bredehorst et al. | |
| 5,462,928 A | 10/1995 | Bachovchin et al. | |
| 5,512,549 A | 4/1996 | Chen et al. | |
| 5,543,396 A | 8/1996 | Powers et al. | |
| 5,580,979 A | 12/1996 | Bachovchin | |
| 5,601,986 A | 2/1997 | Takacs | |
| 5,614,379 A | 3/1997 | MacKellar | |
| 5,614,492 A | 3/1997 | Habener | |
| 5,624,894 A | 4/1997 | Bodor | |
| 5,798,344 A | 8/1998 | Kuroki et al. | |
| 5,811,278 A | 9/1998 | Okamura et al. | |
| 5,811,281 A | 9/1998 | Quaroni et al. | |
| 5,814,460 A | 9/1998 | Venton et al. | |
| 5,885,997 A | 3/1999 | Lohray et al. | |
| 5,939,560 A | 8/1999 | Jenkins et al. | |
| 5,965,532 A | 10/1999 | Bachovchin | |
| 5,985,884 A | 11/1999 | Lohray et al. | |
| 6,006,753 A | 12/1999 | Efendic | |
| 6,011,155 A | 1/2000 | Villhauer | |
| 6,090,786 A | 7/2000 | Augustyns et al. | |
| 6,107,317 A | 8/2000 | Villhauer | |
| 6,110,949 A | 8/2000 | Villhauer | |
| 6,124,305 A | 9/2000 | Villhauer | |
| 6,129,911 A | 10/2000 | Faris | |
| 6,156,739 A | 12/2000 | Griffin et al. | |
| 6,166,063 A | 12/2000 | Villhauer | |
| 6,172,081 B1 | 1/2001 | Damon | |
| 6,184,020 B1 | 2/2001 | Blinkovsky et al. | |
| 6,201,132 B1 | 3/2001 | Jenkins et al. | |
| 6,214,340 B1 | 4/2001 | Takeuchi et al. | |
| 6,235,493 B1 | 5/2001 | Bissell et al. | |
| 6,251,391 B1 | 6/2001 | Wilkinson et al. | |
| 6,258,597 B1 | 7/2001 | Bachovchin et al. | |
| 6,261,794 B1 | 7/2001 | Chang | |
| 6,265,551 B1 | 7/2001 | Duke-Cohan et al. | |
| 6,303,661 B1 | 10/2001 | Demuth et al. | |
| 6,309,868 B1 | 10/2001 | Monod | |
| 6,310,069 B1 | 10/2001 | Lohray et al. | |
| 6,319,893 B1 | 11/2001 | Demuth et al. | |
| 6,325,989 B1 | 12/2001 | Duke-Cohan et al. | |
| 6,335,429 B1 | 1/2002 | Cai et al. | |
| 6,337,069 B1 | 1/2002 | Grouzmann et al. | |
| 6,342,611 B1 | 1/2002 | Weber et al. | |
| 6,355,614 B1 | 3/2002 | Wallner | |
| 6,380,398 B2 | 4/2002 | Kanstrup et al. | |
| 6,395,767 B2 | 5/2002 | Robl et al. | |
| 6,432,969 B1 | 8/2002 | Villhauer | |
| 6,447,772 B1 | 9/2002 | Houston | |
| 6,448,045 B1 | 9/2002 | Levine et al. | |

(Continued)

FOREIGN PATENT DOCUMENTS

DE     21 50 686 A1    4/1973

(Continued)

OTHER PUBLICATIONS

German, et al., Khimicheskoe i Neftyanoe Mashinostroenie, No. 4, pp. 21-23, Apr. 1985.*
Alagarsamy, V. et al. "Synthesis and pharmacological investigation . . . " Pharmazie, vol. 57, No. 5 2002, pp. 306-307, XP008084498.
Algarsamy, V. et al. "Synthesis, analgesic, antii-inflammatory . . . " Bio & Pharm. Bulletin of Japan, Pharma society of JP, vol. 25, No. 11, 2002, pp. 1432-1435, XP008084513 ISSN: 0918-6158.
Desai N C et al "Synthesis and anti-Hiv . . . " Indian Journal of Experimental Bio.,vol. 36, No. 12, 1998 pp. 1280-1283, XP008084509 ISSN: 0019-5889.
Kamata et al., CAPLUS Abstract 105: 191027, 1986 Chemical & Pharma Bulletin (1985), 33(8), 3160-75.
Kotani, T. et al., "Highly selective aldose reductase. . . " Journal of Medicinal Chem., American Chem. Society. Washington, US, vol. 40, No. 5, 1997, pp. 684-694 XP000652330.
Lakhan et al. Journal of Indian Chemical Society (1987), 64 (5), 316-18 (2 pages Abstract).

(Continued)

*Primary Examiner* — Susanna Moore
*Assistant Examiner* — Cecilia M Jaisle
(74) *Attorney, Agent, or Firm* — Mitchell R. Brustein; David M. Stemerick

(57) ABSTRACT

Methods of making polymorphs of the benzoate salt of 2-[[6-[(3r)-3-amino-1-piperidinyl]-3,4-dihydro-3-methyl-2,4-dioxo-1(2h)-pyrimidinyl]methyl]-benzonitrile.

1 Claim, 4 Drawing Sheets

U.S. PATENT DOCUMENTS

| | | |
|---|---|---|
| 6,458,924 B2 | 10/2002 | Knudsen et al. |
| 6,485,955 B1 | 11/2002 | Huber et al. |
| 6,495,544 B2 | 12/2002 | Hansen, Jr. et al. |
| 6,500,804 B2 | 12/2002 | Demuth et al. |
| 6,518,277 B1 | 2/2003 | Sadhu et al. |
| 6,521,644 B1 | 2/2003 | Broqua |
| 6,528,486 B1 | 3/2003 | Larsen et al. |
| 6,545,170 B2 | 4/2003 | Pitzele et al. |
| 6,548,481 B1 | 4/2003 | Demuth et al. |
| 6,548,529 B1 | 4/2003 | Robl et al. |
| 6,555,519 B2 | 4/2003 | Washburn |
| 6,555,521 B2 | 4/2003 | Hermeling et al. |
| 6,559,188 B1 | 5/2003 | Gatlin et al. |
| 6,573,096 B1 | 6/2003 | Chen |
| 6,573,287 B2 | 6/2003 | Sulsky et al. |
| 6,586,198 B2 | 7/2003 | Brown |
| 6,608,038 B2 | 8/2003 | Caplan et al. |
| 6,617,340 B1 | 9/2003 | Villhauer |
| 6,620,821 B2 | 9/2003 | Robl |
| 6,620,910 B1 | 9/2003 | Calas et al. |
| 6,627,636 B2 | 9/2003 | Robl |
| 6,645,995 B2 | 11/2003 | Kanstrup et al. |
| 6,664,273 B2 | 12/2003 | Burnett et al. |
| 6,673,815 B2 | 1/2004 | Devasthale et al. |
| 6,673,829 B2 | 1/2004 | Dorwald et al. |
| 6,686,337 B2 | 2/2004 | Connor |
| 6,699,871 B2 | 3/2004 | Edmondson et al. |
| 6,703,238 B2 | 3/2004 | Bachovchin |
| 6,706,742 B2 | 3/2004 | De Nanteuil et al. |
| 6,710,040 B1 | 3/2004 | Hulin et al. |
| 6,716,843 B2 | 4/2004 | De Nanteuil et al. |
| 6,727,261 B2 | 4/2004 | Gobbi et al. |
| 6,727,271 B2 | 4/2004 | Cheng et al. |
| 6,747,035 B2 | 6/2004 | Guadilliere |
| 6,800,650 B2 | 10/2004 | Boehringer et al. |
| 6,803,357 B1 | 10/2004 | Bachovchin et al. |
| 6,825,169 B1 | 11/2004 | Bachovchin et al. |
| 6,861,440 B2 | 3/2005 | Boehringer et al. |
| 6,867,205 B2 | 3/2005 | Boehringer et al. |
| 6,998,502 B1 | 2/2006 | Majeed |
| 7,125,881 B2 | 10/2006 | Bailey |
| 7,230,000 B1 | 6/2007 | Finer et al. |
| 7,304,086 B2 | 12/2007 | Schilling |
| 7,371,871 B2 | 5/2008 | Schilling |
| 7,470,700 B2 | 12/2008 | Feng |
| 2001/0018210 A1 | 8/2001 | Bachovchin et al. |
| 2001/0020006 A1 | 9/2001 | Demuth et al. |
| 2001/0031780 A1 | 10/2001 | Kanstrup et al. |
| 2001/0047078 A1 | 11/2001 | Chang |
| 2001/0051648 A1 | 12/2001 | Demuth et al. |
| 2002/0006899 A1 | 1/2002 | Pospisilik et al. |
| 2002/0016100 A1 | 2/2002 | Okabe et al. |
| 2002/0019411 A1 | 2/2002 | Robl et al. |
| 2002/0037829 A1 | 3/2002 | Aronson et al. |
| 2002/0041871 A1 | 4/2002 | Brudnak |
| 2002/0049153 A1 | 4/2002 | Bridon et al. |
| 2002/0049164 A1 | 4/2002 | Demuth et al. |
| 2002/0061839 A1 | 5/2002 | Scharpe et al. |
| 2002/0071838 A1 | 6/2002 | Demuth et al. |
| 2002/0077340 A1 | 6/2002 | Sulsky et al. |
| 2002/0082292 A1 | 6/2002 | Sahoo et al. |
| 2002/0082427 A1 | 6/2002 | Demuth et al. |
| 2002/0103242 A1 | 8/2002 | Sahoo et al. |
| 2002/0103384 A1 | 8/2002 | Kanstrup et al. |
| 2002/0110560 A1 | 8/2002 | Demuth et al. |
| 2002/0115843 A1 | 8/2002 | Oi et al. |
| 2002/0132979 A1 | 9/2002 | Chen |
| 2002/0147130 A1 | 10/2002 | Huber et al. |
| 2002/0147157 A1 | 10/2002 | Connor |
| 2002/0155565 A1 | 10/2002 | Garin-Chesa et al. |
| 2002/0164759 A1 | 11/2002 | Travis et al. |
| 2002/0165164 A1 | 11/2002 | Demuth et al. |
| 2002/0169159 A1 | 11/2002 | Medina et al. |
| 2002/0183367 A1 | 12/2002 | Sulsky et al. |
| 2002/0193390 A1 | 12/2002 | Villhauer |
| 2002/0198205 A1 | 12/2002 | Himmelsbach et al. |
| 2002/0198242 A1 | 12/2002 | Demuth et al. |
| 2002/0198380 A1 | 12/2002 | Belzer et al. |
| 2003/0008905 A1 | 1/2003 | Demuth et al. |
| 2003/0008925 A1 | 1/2003 | Demuth et al. |
| 2003/0027282 A1 | 2/2003 | Huber et al. |
| 2003/0040478 A1 | 2/2003 | Drucker et al. |
| 2003/0045464 A1 | 3/2003 | Hermeling et al. |
| 2003/0055052 A1 | 3/2003 | Peters et al. |
| 2003/0060412 A1 | 3/2003 | Prouty et al. |
| 2003/0060434 A1 | 3/2003 | Nielsen et al. |
| 2003/0069234 A1 | 4/2003 | Medina et al. |
| 2003/0087935 A1 | 5/2003 | Cheng et al. |
| 2003/0087950 A1 | 5/2003 | DeNanteuil et al. |
| 2003/0089935 A1 | 5/2003 | Fan et al. |
| 2003/0092630 A2 | 5/2003 | Demuth et al. |
| 2003/0092697 A1 | 5/2003 | Cheng et al. |
| 2003/0096846 A1 | 5/2003 | Cheng et al. |
| 2003/0096857 A1 | 5/2003 | Evans et al. |
| 2003/0100563 A1 | 5/2003 | Edmondson et al. |
| 2003/0103968 A1 | 6/2003 | Amelsberg et al. |
| 2003/0105077 A1 | 6/2003 | Kanstrup et al. |
| 2003/0119736 A1 | 6/2003 | Demuth et al. |
| 2003/0119738 A1 | 6/2003 | Niestroj et al. |
| 2003/0119750 A1 | 6/2003 | Demuth et al. |
| 2003/0125304 A1 | 7/2003 | Demuth et al. |
| 2003/0130199 A1 | 7/2003 | von Hoersten et al. |
| 2003/0130281 A1 | 7/2003 | Boehringer et al. |
| 2003/0130306 A1 | 7/2003 | Devasthale et al. |
| 2003/0134802 A1 | 7/2003 | Demuth et al. |
| 2003/0135023 A1 | 7/2003 | Demuth et al. |
| 2003/0139429 A1 | 7/2003 | Cohen et al. |
| 2003/0139434 A1 | 7/2003 | Balkan et al. |
| 2003/0144206 A1 | 7/2003 | Knudsen et al. |
| 2003/0148961 A1 | 8/2003 | Heiser et al. |
| 2003/0149071 A1 | 8/2003 | Gobbi et al. |
| 2003/0153509 A1 | 8/2003 | Bachovchin et al. |
| 2003/0162820 A1 | 8/2003 | Demuth et al. |
| 2003/0166578 A1 | 9/2003 | Arch et al. |
| 2003/0166662 A1 | 9/2003 | Fryburg et al. |
| 2003/0166690 A1 | 9/2003 | Ebdrup et al. |
| 2003/0171358 A1 | 9/2003 | Jeppesen et al. |
| 2003/0171411 A1 | 9/2003 | Kodra et al. |
| 2003/0176357 A1 | 9/2003 | Pospisilik et al. |
| 2003/0181497 A1 | 9/2003 | Chen et al. |
| 2003/0186963 A1 | 10/2003 | Dorwald et al. |
| 2003/0187254 A1 | 10/2003 | Perry et al. |
| 2003/0191112 A1 | 10/2003 | Dorwald et al. |
| 2003/0195188 A1 | 10/2003 | Boehringer et al. |
| 2003/0195190 A1 | 10/2003 | Peschke et al. |
| 2003/0199451 A1 | 10/2003 | Mogensen et al. |
| 2003/0199528 A1 | 10/2003 | Kanstrup et al. |
| 2003/0199563 A1 | 10/2003 | Robl et al. |
| 2003/0199672 A1 | 10/2003 | Knudsen et al. |
| 2003/0203946 A1 | 10/2003 | Behrens et al. |
| 2003/0216382 A1 | 11/2003 | Boehringer et al. |
| 2003/0216450 A1 | 11/2003 | Evans et al. |
| 2003/0220345 A1 | 11/2003 | Hamby et al. |
| 2003/0225102 A1 | 12/2003 | Sankaranarayanan |
| 2003/0232761 A1 | 12/2003 | Hinke et al. |
| 2003/0236272 A1 | 12/2003 | Carr |
| 2004/0002495 A1 | 1/2004 | Sher et al. |
| 2004/0002609 A1 | 1/2004 | Hulin |
| 2004/0006062 A1 | 1/2004 | Smallheer et al. |
| 2004/0009972 A1 | 1/2004 | Ding et al. |
| 2004/0009998 A1 | 1/2004 | Dhar et al. |
| 2004/0034014 A1 | 2/2004 | Kanstrup et al. |
| 2004/0053369 A1 | 3/2004 | Abbott et al. |
| 2004/0054171 A1 | 3/2004 | Jensen et al. |
| 2004/0058876 A1 | 3/2004 | Hoffmann et al. |
| 2004/0063935 A1 | 4/2004 | Yasuda |
| 2004/0072874 A1 | 4/2004 | Sato et al. |
| 2004/0072892 A1 | 4/2004 | Fukushima et al. |
| 2004/0077645 A1 | 4/2004 | Himmelsbach et al. |
| 2004/0082497 A1 | 4/2004 | Evans et al. |
| 2004/0082607 A1 | 4/2004 | Oi et al. |
| 2004/0087587 A1 | 5/2004 | Himmelsbach et al. |
| 2004/0092478 A1 | 5/2004 | Rothermel et al. |
| 2004/0097510 A1 | 5/2004 | Himmelsbach et al. |
| 2004/0106655 A1 | 6/2004 | Kitajima et al. |
| 2004/0106656 A1 | 6/2004 | Ashton et al. |
| 2004/0106802 A1 | 6/2004 | Sankaranarayanan et al. |

| | | | | | | |
|---|---|---|---|---|---|---|
| 2004/0110817 A1 | 6/2004 | Hulin | EP | 0748800 | | 12/1996 |
| 2004/0116328 A1 | 6/2004 | Yoshikawa et al. | EP | 900568 | | 3/1999 |
| 2004/0132713 A1 | 7/2004 | Hulin et al. | EP | 900568 | A2 | 3/1999 |
| 2004/0132732 A1 | 7/2004 | Han et al. | EP | 900568 | A2 | 10/1999 |
| 2004/0138148 A1 | 7/2004 | Fushimi et al. | EP | 1136482 | A1 | 9/2001 |
| 2004/0138214 A1 | 7/2004 | Himmelsbach et al. | EP | 1197799 | A1 | 4/2002 |
| 2004/0138215 A1 | 7/2004 | Eckhardt et al. | EP | 1229024 | | 8/2002 |
| 2004/0147434 A1 | 7/2004 | Ansorge et al. | EP | 1398032 | | 3/2004 |
| 2004/0152192 A1 | 8/2004 | Bachovchin et al. | EP | 1586571 | | 10/2005 |
| 2004/0152745 A1 | 8/2004 | Jackson et al. | FR | 2 162 106 | | 11/1972 |
| 2004/0166125 A1 | 8/2004 | Himmelsbach et al. | GB | 699812 | | 11/1950 |
| 2004/0167133 A1 | 8/2004 | Edmondson et al. | GB | 1441665 | A | 7/1976 |
| 2004/0167191 A1 | 8/2004 | Demuth et al. | GB | 1464248 | A | 2/1977 |
| 2004/0167341 A1 | 8/2004 | Haffner et al. | GB | 2143542 | | 2/1985 |
| 2004/0171104 A1 | 9/2004 | Blinkovsky et al. | GB | 2143542 | A | 2/1985 |
| 2004/0171555 A1 | 9/2004 | Demuth et al. | GB | 2230527 | A | 10/1990 |
| 2004/0171848 A1 | 9/2004 | Haffner et al. | JP | 53005180 | A | 1/1978 |
| 2004/0176406 A1 | 9/2004 | Gobbi et al. | JP | 9295977 | | 11/1997 |
| 2004/0176428 A1 | 9/2004 | Edmondson et al. | JP | 2002/338466 | | 11/2002 |
| 2004/0180925 A1 | 9/2004 | Matsuno et al. | JP | 2003/128551 | | 5/2003 |
| 2004/0186153 A1 | 9/2004 | Yasuda et al. | JP | 2004/99600 | A | 4/2004 |
| 2004/0198786 A1 | 10/2004 | Gretzke et al. | JP | 2004/123738 | A | 4/2004 |
| 2004/0209891 A1 | 10/2004 | Broqua et al. | WO | WO 89/10701 | | 11/1989 |
| 2004/0229820 A1 | 11/2004 | Bachovchin et al. | WO | WO 91/11457 | | 8/1991 |
| 2004/0229848 A1 | 11/2004 | Demuth et al. | WO | WO 91/12001 | | 8/1991 |
| 2004/0236102 A1 | 11/2004 | Brockunier et al. | WO | WO 93/21162 | | 1/1993 |
| 2004/0242566 A1 | 12/2004 | Feng et al. | WO | WO 93/08259 | A3 | 4/1993 |
| 2004/0242568 A1 | 12/2004 | Feng et al. | WO | WO 93/24634 | | 12/1993 |
| 2004/0242636 A1 | 12/2004 | Haffner et al. | WO | WO 94/03055 | | 2/1994 |
| 2004/0242898 A1 | 12/2004 | Hulin et al. | WO | WO 95/15309 | | 6/1995 |
| 2004/0254167 A1 | 12/2004 | Biftu et al. | WO | WO 95/29691 | | 11/1995 |
| 2004/0254226 A1 | 12/2004 | Feng et al. | WO | WO 95/35031 | | 12/1995 |
| 2004/0259843 A1 | 12/2004 | Madar et al. | WO | WO 96/02667 | | 2/1996 |
| 2004/0259859 A1 | 12/2004 | Feng et al. | WO | WO 96/32384 | | 10/1996 |
| 2004/0259883 A1 | 12/2004 | Sakashita et al. | WO | WO 96/38550 | | 12/1996 |
| 2004/0259902 A1 | 12/2004 | Boehringer et al. | WO | WO 97/40832 | | 11/1997 |
| 2004/0259903 A1 | 12/2004 | Boehringer et al. | WO | WO 98/00439 | A2 | 1/1998 |
| 2004/0259919 A1 | 12/2004 | Magnin et al. | WO | WO 98/00439 | A3 | 1/1998 |
| 2005/0004117 A1 | 1/2005 | Feng et al. | WO | WO 98/18763 | | 5/1998 |
| 2005/0014732 A1 | 1/2005 | Gulve et al. | WO | WO 98/19998 | | 5/1998 |
| 2005/0014946 A1 | 1/2005 | Demuth et al. | WO | WO 98/24780 | | 6/1998 |
| 2005/0020574 A1 | 1/2005 | Hauel et al. | WO | WO 98/50046 | | 11/1998 |
| 2005/0026921 A1 | 2/2005 | Eckhardt et al. | WO | WO 98/51803 | | 11/1998 |
| 2005/0032804 A1 | 2/2005 | Cypes et al. | WO | WO 99/02705 | | 1/1999 |
| 2005/0038020 A1 | 2/2005 | Hamann et al. | WO | WO 99/16864 | | 4/1999 |
| 2005/0043292 A1 | 2/2005 | Parker et al. | WO | WO 99/17799 | | 4/1999 |
| 2005/0043299 A1 | 2/2005 | Evans et al. | WO | WO 99/18856 | | 4/1999 |
| 2005/0058635 A1 | 3/2005 | Demuth et al. | WO | WO 99/28474 | | 6/1999 |
| 2005/0065144 A1 | 3/2005 | Feng et al. | WO | WO 99/38501 | A2 | 8/1999 |
| 2005/0065145 A1 | 3/2005 | Cao et al. | WO | WO 99/38501 | A3 | 8/1999 |
| 2005/0065148 A1 | 3/2005 | Feng et al. | WO | WO 99/46272 | | 9/1999 |
| 2005/0070530 A1 | 3/2005 | Feng et al. | WO | WO 99/47152 | | 9/1999 |
| 2005/0070531 A1 | 3/2005 | Feng et al. | WO | WO 99/50249 | A2 | 10/1999 |
| 2005/0070535 A1 | 3/2005 | Feng et al. | WO | WO 99/50249 | A3 | 10/1999 |
| 2005/0070706 A1 | 3/2005 | Feng et al. | WO | WO 99-61431 | | 12/1999 |
| 2005/0075330 A1 | 4/2005 | Feng et al. | WO | WO 99/62914 | | 12/1999 |
| 2005/0261271 A1 | 11/2005 | Feng et al. | WO | WO 99/67278 | | 12/1999 |
| 2006/0135767 A1 | 6/2006 | Feng et al. | WO | WO 99/67279 | | 12/1999 |
| 2007/0060528 A1 | 3/2007 | Feng et al. | WO | WO 00/07617 | | 2/2000 |
| 2007/0060530 A1 | 3/2007 | Feng et al. | WO | WO 00/09666 | A2 | 2/2000 |
| 2008/0003283 A1 | 1/2008 | Feng et al. | WO | WO 00/09666 | A3 | 2/2000 |
| 2008/0108807 A1 | 5/2008 | Feng et al. | WO | WO 00/10549 | | 3/2000 |
| 2008/0108808 A1 | 5/2008 | Feng et al. | WO | WO 00/15211 | A2 | 3/2000 |
| | | | WO | WO 00/15211 | A3 | 3/2000 |
| | FOREIGN PATENT DOCUMENTS | | WO | WO 00/20416 | | 4/2000 |
| DE | 2361551 A1 | 6/1975 | WO | WO 00/76986 | A1 | 4/2000 |
| DE | 2500024 A1 | 7/1976 | WO | WO 00/34241 | | 6/2000 |
| DE | 2801289 A1 | 5/1979 | WO | WO 00/40583 | | 7/2000 |
| DE | 2801289 C2 | 5/1979 | WO | WO 00/43366 | | 7/2000 |
| DE | 10256264 A | 6/2004 | WO | WO 00/47219 | A2 | 8/2000 |
| EP | 0378255 A2 | 7/1990 | WO | WO 00/47219 | A3 | 8/2000 |
| EP | 0 442 473 A | 8/1991 | WO | WO 00/53171 | | 9/2000 |
| EP | 0505893 | 9/1992 | WO | WO 00/56296 | A2 | 9/2000 |
| EP | 0547442 A1 | 6/1993 | WO | WO 00/56296 | A3 | 9/2000 |
| EP | 0547514 | 6/1993 | WO | WO 00/56297 | | 9/2000 |
| EP | 0574846 | 12/1993 | WO | WO 00/57721 | A2 | 10/2000 |
| EP | 0587377 A2 | 3/1994 | WO | WO 00/57721 | A3 | 10/2000 |
| EP | 0657452 | 6/1995 | WO | WO 01/14318 | A2 | 3/2001 |
| EP | 0702013 | 3/1996 | WO | WO 01/14318 | A3 | 3/2001 |

| | | | | | | |
|---|---|---|---|---|---|---|
| WO | WO 01/16301 | | 3/2001 | WO | WO 03/011814 | 2/2003 |
| WO | WO 01/19866 | | 3/2001 | WO | WO 03/011892 A2 | 2/2003 |
| WO | WO 01/23364 | A1 | 4/2001 | WO | WO 03/011892 A3 | 2/2003 |
| WO | WO 01/34594 | A1 | 5/2001 | WO | WO 03/014318 A2 | 2/2003 |
| WO | WO 01/40180 | A2 | 6/2001 | WO | WO 03/014318 A3 | 2/2003 |
| WO | WO 01/40180 | A3 | 6/2001 | WO | WO 03/015775 | 2/2003 |
| WO | WO 01/52825 | A2 | 7/2001 | WO | WO 03/016335 A2 | 2/2003 |
| WO | WO 01/52825 | A3 | 7/2001 | WO | WO 03/016335 A3 | 2/2003 |
| WO | WO 01/55105 | | 8/2001 | WO | WO 03/017936 A2 | 3/2003 |
| WO | WO 01/55119 | | 8/2001 | WO | WO 03/017936 A3 | 3/2003 |
| WO | WO 01/56988 | A1 | 8/2001 | WO | WO 03/022871 A2 | 3/2003 |
| WO | WO 01/62266 | A2 | 8/2001 | WO | WO 03/024942 | 3/2003 |
| WO | WO 01/62266 | A3 | 8/2001 | WO | WO 03/024965 A2 | 3/2003 |
| WO | WO 01/68603 | A2 | 9/2001 | WO | WO 03/024965 A3 | 3/2003 |
| WO | WO 01/68603 | A3 | 9/2001 | WO | WO 03/053330 A2 | 3/2003 |
| WO | WO 01/70729 | A1 | 9/2001 | WO | WO 03/053330 A3 | 3/2003 |
| WO | WO 01/72290 | A2 | 10/2001 | WO | WO 03/026652 A1 | 4/2003 |
| WO | WO 01/72290 | A3 | 10/2001 | WO | WO 03/027080 A1 | 4/2003 |
| WO | WO 01/74299 | | 10/2001 | WO | WO 03/030946 A1 | 4/2003 |
| WO | WO 01/79206 | | 10/2001 | WO | WO 03/033524 A2 | 4/2003 |
| WO | WO 01/81304 | | 11/2001 | WO | WO 03/033524 A3 | 4/2003 |
| WO | WO 01/81337 | | 11/2001 | WO | WO 03/033671 A2 | 4/2003 |
| WO | WO 01/89569 | | 11/2001 | WO | WO 03/035057 A1 | 5/2003 |
| WO | WO 01/94597 | | 12/2001 | WO | WO 03/035067 | 5/2003 |
| WO | WO 01/96295 | A2 | 12/2001 | WO | WO 03/035640 A1 | 5/2003 |
| WO | WO 01/97808 | A1 | 12/2001 | WO | WO 03/037327 | 5/2003 |
| WO | WO 02/02560 | A2 | 1/2002 | WO | WO 03/037888 A1 | 5/2003 |
| WO | WO 02/04610 | | 1/2002 | WO | WO 03/038123 | 5/2003 |
| WO | WO 02/08931 | | 1/2002 | WO | WO 03/040114 | 5/2003 |
| WO | WO 02/09716 | A | 2/2002 | WO | WO 03/040174 A2 | 5/2003 |
| WO | WO 02/14271 | | 2/2002 | WO | WO 03/040174 A3 | 5/2003 |
| WO | WO 02/20488 | A2 | 3/2002 | WO | WO 03/045228 A2 | 6/2003 |
| WO | WO 02/20804 | | 3/2002 | WO | WO 03/045228 A3 | 6/2003 |
| WO | WO 02/26703 | | 4/2002 | WO | WO 03/045977 A2 | 6/2003 |
| WO | WO 02/28742 | | 4/2002 | WO | WO 03/045977 A3 | 6/2003 |
| WO | WO 02/30890 | | 4/2002 | WO | WO 03/048081 A2 | 6/2003 |
| WO | WO 02/30891 | A1 | 4/2002 | WO | WO 03/048081 A3 | 6/2003 |
| WO | WO 02/30891 | C1 | 4/2002 | WO | WO 03/048158 A1 | 6/2003 |
| WO | WO 02/31134 | | 4/2002 | WO | WO 03/051848 A2 | 6/2003 |
| WO | WO 02/34242 | A2 | 5/2002 | WO | WO 03/051848 A3 | 6/2003 |
| WO | WO 02/34242 | A3 | 5/2002 | WO | WO 03/055881 | 7/2003 |
| WO | WO 02/34900 | | 5/2002 | WO | WO 03/057144 A2 | 7/2003 |
| WO | WO 02/38541 | | 5/2002 | WO | WO 03/057144 A3 | 7/2003 |
| WO | WO 02/38742 | A2 | 5/2002 | WO | WO 03/057200 A2 | 7/2003 |
| WO | WO 02/38742 | A3 | 5/2002 | WO | WO 03/057666 A2 | 7/2003 |
| WO | WO 02/051836 | | 7/2002 | WO | WO 03/057666 A3 | 7/2003 |
| WO | WO 02/053170 | A2 | 7/2002 | WO | WO 03/063903 A2 | 8/2003 |
| WO | WO 02/053170 | A3 | 7/2002 | WO | WO 03/065983 A2 | 8/2003 |
| WO | WO 02/059301 | | 8/2002 | WO | WO 03/065983 A3 | 8/2003 |
| WO | WO 02/059343 | A2 | 8/2002 | WO | WO 03/068748 | 8/2003 |
| WO | WO 02/059343 | A3 | 8/2002 | WO | WO 03/068757 A1 | 8/2003 |
| WO | WO 02/062764 | | 8/2002 | WO | WO 03/072197 | 9/2003 |
| WO | WO 02/066627 | | 8/2002 | WO | WO 03/072556 A1 | 9/2003 |
| WO | WO 02/068420 | | 9/2002 | WO | WO 03/074500 A2 | 9/2003 |
| WO | WO 02/076450 | | 10/2002 | WO | WO 03/074500 A3 | 9/2003 |
| WO | WO 02/083109 | A1 | 10/2002 | WO | WO 03/076393 | 9/2003 |
| WO | WO 02/083128 | | 10/2002 | WO | WO 03/076414 | 9/2003 |
| WO | WO 02/092127 | | 11/2002 | WO | WO 03/076418 A1 | 9/2003 |
| WO | WO 02/094178 | A2 | 11/2002 | WO | WO 03/077935 | 9/2003 |
| WO | WO 02/096357 | A2 | 12/2002 | WO | WO 03/080070 A2 | 10/2003 |
| WO | WO 02/096357 | A3 | 12/2002 | WO | WO 03/080070 A3 | 10/2003 |
| WO | WO 03/000180 | A2 | 1/2003 | WO | WO 03/080633 | 10/2003 |
| WO | WO 03/000180 | A3 | 1/2003 | WO | WO 03/082817 A2 | 10/2003 |
| WO | WO 03/000181 | A2 | 1/2003 | WO | WO 03/082817 A3 | 10/2003 |
| WO | WO 03/000250 | A1 | 1/2003 | WO | WO 03/082859 | 10/2003 |
| WO | WO 03/000250 | A3 | 1/2003 | WO | WO 03/082898 A2 | 10/2003 |
| WO | WO 03/002530 | | 1/2003 | WO | WO 03/082898 A3 | 10/2003 |
| WO | WO 03/002531 | | 1/2003 | WO | WO 03/084940 A1 | 10/2003 |
| WO | WO 03/002553 | | 1/2003 | WO | WO 03/084940 B1 | 10/2003 |
| WO | WO 03/002596 | A2 | 1/2003 | WO | WO 03/092605 A2 | 11/2003 |
| WO | WO 03/002596 | A3 | 1/2003 | WO | WO 03/092605 A3 | 11/2003 |
| WO | WO 03/004496 | | 1/2003 | WO | WO 03/099279 A1 | 12/2003 |
| WO | WO 03/004498 | | 1/2003 | WO | WO 03/099286 | 12/2003 |
| WO | WO 03/007888 | A2 | 1/2003 | WO | WO 03/099818 A1 | 12/2003 |
| WO | WO 03/010197 | A2 | 2/2003 | WO | WO 03/101449 A2 | 12/2003 |
| WO | WO 03/010197 | A3 | 2/2003 | WO | WO 03/101449 A3 | 12/2003 |
| WO | WO 03/010314 | A2 | 2/2003 | WO | WO 03/101958 A2 | 12/2003 |
| WO | WO 03/010314 | A3 | 2/2003 | WO | WO 03/101958 A3 | 12/2003 |
| WO | WO 03/011807 | | 2/2003 | WO | WO 03/104207 A2 | 12/2003 |

| | | |
|---|---|---|
| WO | WO 03/104207 A3 | 12/2003 |
| WO | WO 03/104208 | 12/2003 |
| WO | WO 03/104229 | 12/2003 |
| WO | WO 03/106416 A2 | 12/2003 |
| WO | WO 03/106416 A3 | 12/2003 |
| WO | WO 03/106456 A2 | 12/2003 |
| WO | WO 03/106456 A3 | 12/2003 |
| WO | WO 2004/002535 A1 | 1/2004 |
| WO | WO 2004/002535 C1 | 1/2004 |
| WO | WO 2004/002986 A2 | 1/2004 |
| WO | WO 2004/002986 A3 | 1/2004 |
| WO | WO 2004/004655 A2 | 1/2004 |
| WO | WO 2004/004655 A3 | 1/2004 |
| WO | WO 2004/004661 A2 | 1/2004 |
| WO | WO 2004/004661 A3 | 1/2004 |
| WO | WO 2004/004665 A2 | 1/2004 |
| WO | WO 2004/004665 A3 | 1/2004 |
| WO | WO 2004/007446 | 1/2004 |
| WO | WO 2004/007468 | 1/2004 |
| WO | WO 2004/014860 A3 | 1/2004 |
| WO | WO 2004/011640 | 2/2004 |
| WO | WO 2004/014860 A2 | 2/2004 |
| WO | WO 2004/017989 A1 | 3/2004 |
| WO | WO 2004/018467 A2 | 3/2004 |
| WO | WO 2004/018467 A3 | 3/2004 |
| WO | WO 2004/018468 A2 | 3/2004 |
| WO | WO 2004/018468 A3 | 3/2004 |
| WO | WO 2004/018469 | 3/2004 |
| WO | WO 2004/020407 | 3/2004 |
| WO | WO 2004/024184 | 3/2004 |
| WO | WO 2004/026822 A2 | 4/2004 |
| WO | WO 2004/026822 A3 | 4/2004 |
| WO | WO 2004/028524 | 4/2004 |
| WO | WO 2004/031175 A2 | 4/2004 |
| WO | WO 2004/031175 A3 | 4/2004 |
| WO | WO 2004/031374 A2 | 4/2004 |
| WO | WO 2004/031374 A3 | 4/2004 |
| WO | WO 2004/032836 A2 | 4/2004 |
| WO | WO 2004/032836 A3 | 4/2004 |
| WO | WO 2004/032861 A2 | 4/2004 |
| WO | WO 2004/032861 A3 | 4/2004 |
| WO | WO 2004/033455 A2 | 4/2004 |
| WO | WO 2004/033455 A3 | 4/2004 |
| WO | WO 2004/037169 A2 | 5/2004 |
| WO | WO 2004/037169 A3 | 5/2004 |
| WO | WO 2004/037176 A2 | 5/2004 |
| WO | WO 2004/037176 A3 | 5/2004 |
| WO | WO 2004/037181 A2 | 5/2004 |
| WO | WO 2004/037181 A3 | 5/2004 |
| WO | WO 2004/041795 | 5/2004 |
| WO | WO 2004/043940 | 5/2004 |
| WO | WO 2004/046106 | 6/2004 |
| WO | WO 2004/048352 A2 | 6/2004 |
| WO | WO 2004/048352 A3 | 6/2004 |
| WO | WO 2004/050022 A2 | 6/2004 |
| WO | WO 2004/050022 A3 | 6/2004 |
| WO | WO 2004/050022 B1 | 6/2004 |
| WO | WO 2004/050022 C1 | 6/2004 |
| WO | WO 2004/050656 | 6/2004 |
| WO | WO 2004/050658 | 6/2004 |
| WO | WO 2004/052850 A2 | 6/2004 |
| WO | WO 2004/052850 A3 | 6/2004 |
| WO | WO 2004/058266 | 7/2004 |
| WO | WO 2004/062613 A2 | 7/2004 |
| WO | WO 2004/064778 A2 | 8/2004 |
| WO | WO 2004/064778 A3 | 8/2004 |
| WO | WO 2004/067509 | 8/2004 |
| WO | WO 2004/069162 A2 | 8/2004 |
| WO | WO 2004/069162 A3 | 8/2004 |
| WO | WO 2004/071454 A2 | 8/2004 |
| WO | WO 2004/071454 A3 | 8/2004 |
| WO | WO 2004/075815 A2 | 9/2004 |
| WO | WO 2004/075815 A3 | 9/2004 |
| WO | WO 2004/075891 | 9/2004 |
| WO | WO 2004/076401 | 9/2004 |
| WO | WO 2004/076433 | 9/2004 |
| WO | WO 2004/076434 | 9/2004 |
| WO | WO 2004/078777 A2 | 9/2004 |
| WO | WO 2004/078777 A3 | 9/2004 |
| WO | WO 2004/080958 A2 | 9/2004 |
| WO | WO 2004/080958 A3 | 9/2004 |
| WO | WO 2004/082599 A2 | 9/2004 |
| WO | WO 2004/083212 | 9/2004 |
| WO | WO 2004/085408 A1 | 10/2004 |
| WO | WO 2004/085661 A2 | 10/2004 |
| WO | WO 2004/085661 A3 | 10/2004 |
| WO | WO 2004/087053 A3 | 10/2004 |
| WO | WO 2004/087053 C2 | 10/2004 |
| WO | WO 2004/087650 A2 | 10/2004 |
| WO | WO 2004/087650 A3 | 10/2004 |
| WO | WO 2004/087880 A2 | 10/2004 |
| WO | WO 2004/087880 A3 | 10/2004 |
| WO | WO 2004/087880 C1 | 10/2004 |
| WO | WO 2004/089362 | 10/2004 |
| WO | WO 2004/096806 | 11/2004 |
| WO | WO 2004/098625 | 11/2004 |
| WO | WO 2004/099134 | 11/2004 |
| WO | WO 2004/099185 | 11/2004 |
| WO | WO 2004/101514 | 11/2004 |
| WO | WO 2004/103276 A2 | 12/2004 |
| WO | WO 2004/103276 A3 | 12/2004 |
| WO | WO 2004/103993 | 12/2004 |
| WO | WO 2004/104215 | 12/2004 |
| WO | WO 2004/104216 | 12/2004 |
| WO | WO 2004/110436 | 12/2004 |
| WO | WO 2004/111041 | 12/2004 |
| WO | WO 2004/111051 | 12/2004 |
| WO | WO 2004/112701 A2 | 12/2004 |
| WO | WO 2004/112701 A3 | 12/2004 |
| WO | WO 2005/000846 | 1/2005 |
| WO | WO 2005/003135 | 1/2005 |
| WO | WO 2005/004906 A2 | 1/2005 |
| WO | WO 2005/011581 A2 | 2/2005 |
| WO | WO 2005/011581 A3 | 2/2005 |
| WO | WO 2005/012249 A2 | 2/2005 |
| WO | WO 2005/012249 A3 | 2/2005 |
| WO | WO 2005/016911 | 2/2005 |
| WO | WO 2005/019168 A2 | 3/2005 |
| WO | WO 2005/019168 A3 | 3/2005 |
| WO | WO 2005/095381 | 10/2005 |
| WO | WO 2007/033265 | 3/2007 |

OTHER PUBLICATIONS

Misra, V. et al. "Synthesis of N-aryl-n . . . " Pol. J. Pharmacol Pharm vol. 31, 1979, pp. 161-167, XP008084507.

Miyamura, K. et al. "Reaction of Copper (II) Complexes Optically . . . " J. Chem. Soc. Dalton Trans. 1987, pp. 1127-1132, XP008082357.

Schilling et al., CAPLUS 2005:1050865 DN 143:347172.

Sederaviciute et al., CAPLUS Abstract 125:300937 (1996).

Shyam et al. Current Science (1975), 44(16), 572-4 (one page abstract).

Tiwari et al. Indian Journal of Pharmaceutical Science (1978), 40(2), 40-3 (2 pages abstract).

Wang et al. "Studies of Quinazolinones . . . " Biorganic & Med hem.. Letters, Oxford, GB, vol. 12, No. 4, 2002, pp. 571-574, XP009077496 ISSN 0960-894X.

Abdel-Fattah et al. Indian Journal of Heterocyclic Chemistry (1999), 8(3), 177-182. (Abstract, 2 pages).

Adel Hamid et al. Scientia Pharmaceutica (2001), 69(4), 351-366.

Abdel-Rahman, R. M.: Synthesis of some new fluorine bearing trisubstituted 3-thioxo-1, 2, 4-triazin-5-ones as potential anticancer agents: Farmaco, Edizione Scientifica, Societa Chimica Italiana, Pavia, IT, vol. 47, No. 3 (Mar. 1992), pp. 319-326, XP008000322.

Akahoshi, F. et al.: "Synthesis and pharmacological activitey of triazolo[1,5-a]triazine derivatives inhibiting eosinophilia." Journal of Medicinal Chemistry, vol. 41, No. 16, (Jul. 30, 1998), pp. 2985-2993, XP002390903.

Argaud, Doriane et al., Metaformin decreases gluconeogenesis by enhancing the pyruvate kinase flux in isolated rat hepatocytes, European J. Biochem. 213, 1341-1348 (1993).

Ashcroft, Stephen J.H. et al., Structure-activity relationships of alloxan-like compounds derived from uric acid, Br. J. Pharmac. (1986), 89 pp. 469-472.

Baker, B.R. et al., Irreversible Enzyme Inhibitors. On the Mode of Pyrimidine Binding of 5-alkyl and 5-Arylpyrimidines to Dihydrofolic Reductase (1,2), Journal of Heterocyclic Chemistry vol. 4 (1967) pp. 39-48.

Banker, G.S. et al, "Modern Pharmaceutices, 3rd edition", Marcel Dekker, New York, 1996, pp. 451 and 596.

Bal, Gunther, Dipeptidyl Peptidase IV and Prolyl Oligopeptidase: Design, Synthesis and Evaluation of Substrates and Inhibitors, (2002) Universiteit Antwerpen.

Barakat, S.E.S., Synthesis and hypoglycemic activity of some new 3-[4- [[[(cyclohexylamino) carbonyl] amino]sulfony]phenyl]-4(3H)-quinazolinones, Az. J. Pharm. Sci., vol. 25, (2000), pp. 48-57.

Barakat, S.E.S., Synthesis and Hypoglycemic Activity of Some New 4(3H) -Quinazolinone Analogues, Saudi Pharmaceutical Journal, vol. 8, No. 4 (2000) pp. 198-204.

Barnela et al. Indian Journal of Chemistry Section B: Organic Chemistry Including Medicinal Chemistry (1986), 25B(7), 709-11. (Abstract 2 pages).

Belgodere, Elena et al., Synthesis of Substituted Pyrimidines, Study of the Structure and of the Tautomeric Equilibria, (1976) Chem. Abstracts, Columbus, OH vol. 85 No. 9.

Bezuglyi, P.O. et al., Synthesis of arylsulfonyl hydrazide of 3-R-quinazolone-4-carbonyl-2-acid, Pharmaceutical Journal (1979), pp. 70-71.

Bhaduri, A.P. et al., Urinary Metabolite of 2-Piperazino-3 (H)-4-Quinazolone (Centpiperalone), A Potent Blood Sugar Lowering Agent, Indian J. Biochem. Biophys., vol. 12 (1975), pp. 413-414.

Borrell, J. I. et al.: "Synthesis, structure and cytotoxicity evaluation of palladium(II) complexes of 4-amino-3-hydrazino-1,2,4-triazin-5(4h)-on es and 4-amino-3-(n-methylhydrazino)-1,2,4-triazi N-5(4H)-ones" Anales De Quimica, vol. 91, No. 3/4, 1995, pp. 243-252, XP008000323.

Botta, M., Saladino, R., Lamba, D. Nicoletti, R.: Researches on Antiviral Agents. 31. Synthesis and Transformations of Racemic and Chiral 6-Oxiranyl Pyrimidinones, Tetrahedron, vol. 49, 1993, pp. 6053-6070, XP002329846.

Bouras, Mohammed, et al., Metabolism of enterostatin in rat intestine, brain, membranes and serum: differential involvement of proline-specific peptidases, Peptides, vol. 16, No. 3, (1995), pp. 399-405.

Brun, Jean-Frederic, et al., Effects of Oral Zinc Gluconate on Glucose Effectiveness and Insulin Sensitivity in Humans, Biological Trace Element Research vol. 47 (1995), pp. 385-391.

Buckley, DI, Analysis of the Degradation of Insulinotropin [GLP-1 (7-37)] in Human Plasma and Production of Degradation Resistant Analogs.

Buysens, K. J. et al.: "Synthesis of New Pyrrolo[3,4-b]- and [3,4-c]pyridin(on)es and related 1,7-Naphthyridinones and 2,7-naphthyridines via intramolecular diels-alder reactions of 2(1H)-pyrazinones" Tetrahedron, Elsevier Science Publishers, Amsterdam, NL, vol. 52, No. 27, (Jul. 1, 1996), pp. 9161-9178, XP004104003.

Cecil Textbook of Medicine, edited by Bennet, J.C., and Plum F., 20th edition, vol. 1, 1004-10, 1996.

Chatterjee, A.K. et al., Effect of Centpiperalone in Insulin Deficient Diabetes, Indian Journal of Experimental Biology vol. 18 (1980), pp. 1005-1008.

Chatterjee, A.K. et al., Effect of Centpiperalone, a New Hypoglycemic Agent on Insulin Biosynthesis & Release from Isolated Pancreatic Islets of Rat, Indian Journal of Experimental Biology vol. 20 (1981) pp. 270-272.

Chenard et al. J. Med Chem. 2001, 44, 1710-1717.

Caira M R: "Crystalline Polymorphism of Organic Compounds" Topics in Current Chemistry, Springer, Berlin, DE, vol. 198, 1998, pp. 163-208, XP001156954 ISSN: 0340-1022 p. 165.

Coppola, Gary M. et al., 1-Aminomethylisoquinoline-4-carboxylates as Novel Dipeptidylpeptidase IV Inhibitors, Bioorganic & Medicinal Chemistry Letters vol. 10 (2000), pp. 1555-1558.

Deacon, Carolyn F. et al., Both Subcutaneously and Intravenously Administered Glucagon-Like Peptide I Are Rapidly Degraded From the $NH_2$-Terminus in Type II Diabetic Patients and in Healthy Subjects, Diabetes, vol. 44 (1996), pp. 1125-1131.

Deacon, Carolyn F. et al., Degradation of Glucagon-Like Peptide 1 in Vitro Yields an N-Terminally Truncated Peptide That is a Major Endogenous Metabolite in Vivo, Journal of Clinical Endocrinology and Metabolism vol. 80, No. 3 (1995), pp. 952-957.

Deacon, Carolyn F. et al., Dipeptidyl peptidase IV Inhibition as an Approach to the Treatment and Prevention of Type 2 Diabetes: a Historical Perspective, Biochemical and Biophysical Research Communications 294 (2002), pp. 1-4.

Deacon, Carolyn F. et al., Dipeptidyl peptidase IV Inhibition Influences GLP-1 Metabolism in Vivo, Regulatory Peptides vol. 64 Issues 1-3 (1996) p. 30.

Deacon, Carolyn F. et al., Dipeptidyl peptidase IV Inhibition Potentiates the Insulinotropic Effect of Glucagon-Like Peptide 1 in the Anesthetized Pig, Diabetes, vol. 47 (1998), pp. 764-769.

Demuth, Hans-Ulrich et al., Rebuttal to Deacon and Hoist: "Metaformin effects on depeptidyl peptidase IV degradation of glucagons-like peptide-1" versus "dipeptidyl peptidase inhibition as an approach to the treatment and prevention of type 2 diabetes: a historical perspective" Biochemical and Biophysical Research Communications 296 (2002) pp. 229-232.

Dey, Paramita D., et al., Regioselective [4+2] Cycloaddition versus Nucleophilic Reactions of N-Arylamino Substituted 1,3-Diaza-1,3-Butadienes with Ketenes: Synthesis of Pyrimidinone and Fused Pyrimidione Derivatives. Part II. Tetrahedron, vol. 53, No. 40, pp. 13829-13840, 1997.

Dumas, Donald J. "Total synthesis of peramine" Journal of Organic Chemistry, American Chemical Society, Easton, US, vol. 5, 1988, pp. 4650-4653, XP002087391.

Engel, Michael et al., The crystal structure of dipeptidyl peptidase IV (CD26) reveals its functional regulation and enzymatic mechanism, Proc. Nat. Acad. Sci. Early Edition (2003), pp. 1-6.

Fraisse, L., et al. Long-Chained Substituted Uric Acid and 5,6-Diaminouracil Derivatives as Novel Agents against Free Radical Processes: Synthesis and in Vitro Activity, Journal of Medicinal Chemistry, vol. 36, 1993, pp. 1456-1473, XP002329847.

Fraser & Kermack "The Reaction of Paludrine (Proguanil) with Ethyl Acetoacetate" 1951 pp. 2682-2686.

Garratt, Peter J. et al., A Novel Synthesis of Dihydropyrimidines, J. Chem. Soc., Chem. Commun. (1987), pp. 568-569.

Garratt, Peter J. et al., One-Carbon Compounds as Synthetic Intermediates. The Synthesis of Hydropyrimidines and Hydroquinazolines by Sequential Nucleophilic Addition to Diphenyl Cyanocarbonimidate With Concomitant Cyclization, J. Org. Chem. (1988), pp. 1062-1069.

Gazit, Aviv et al., Tyrphostins IV—Highly Potent Inhibitors of EGF Receptor Kinase. Structure-Activity Relationship Study of 4-Anilidoquinazolines, Bioorganic & Medicinal Chemistry, vol. 4, No. 8 (1996) pp. 1203-1207.

Green et al., Expert Opin. Emergin Drugs, 11(3); 525-539, 2006.

Guerrieri, N., et al., Vanadium Inhibition of Serine and Cysteine Proteases, Comparative Biochemistry and Physiology Part A 122 (1997), pp. 331-336.

Gupta, A. et al.: "Fluorine containing Biologically Active Agents: Synthesis of some new Pyrimidine Derivatives" J.Ind. Chem.Soc., vol. 71 1994, pp. 635-636, XP000889664 compound 1.

Gupta, C.M. et al., A Novel Class of Hypoglycaemic Agents: Syntheses & SAR in 2-Substituted 4(3H)-Quinazolones, 2-Substituted 4-Hydroxypolymethylene 5,6]pyrimidines & 3-Substituted 4-Oxopyrido [I,2-a] pyrimidines, Indian Journal of Chemistry, vol. 9 (1971), pp. 201-206.

Gupta, C.M. et al., Drugs Acting on the Central Nervous System. Syntheses of Substituted Quinazolones and Quinazolines and Triazepino-and Triazocionquinazolones, Division of Medicinal Chemistry, Central Drug Research Institute, Lucknow, India (1968), pp. 392-395.

Gupta, C.M. et al., New Potent Blood Sugar Lowering Compound, Nature, vol. 223 (1969), p. 524.

Hermecz, Istvan et al., Pyrido[1,2-a]Pyrimidines; New Chemical Entities in Medicinal Chemistry, Medicinal Research Reviews, vol. 8, No. 2 (1988) pp. 203-230.

Hinke, Simon A. et al., Metaformin Effects on Dipeptidylpeptidase IV Degradation of Glucagon-like Peptide-1, Biochemical and Biophysical Research Communications, 291 (2002) pp. 1302-1308.

Hinke, Simon A. et al., On Combination Therapy of Diabetes With Metaformin and Dipeptidyl Peptidase IV Inhibitors, Diabetes Care, vol. 25, No. 8 (2002) pp. 1490-1492.

Holz, George G. et al, Pancreatic Beta-Cells are Rendered Glucose-Competent by the Insulinotropic Hormone Glucagon-Like Peptide-1(7-37), Nature, vol. 361 (1993), pp. 362-365.

Jakubkiene, Virginija, et al., (G-Methyl-2methylsulfanyl-4-oxo-3,4-dihydro-3-pyrimidinyl)acetic acid and related compounds exhibiting anti-inflammatory activity. Pharmazie 57 (2002) 9, pp. 610-613.

Jones, Terence R., et al., Azafluorenes Containing Two Bridgehead Nitrogen Atoms. Journal of the Chemical Society, Perkin Transactions 1, No. 12, Dec. 1987, pp. 2585-2592.

Kesarwani, A. P. et al.: Solid-phase synthesis of quinazolin-(3H)-ones with three-point diversity, Tetrahedron Letters, vol. 43, (2002) pp. 5579-5581.

Khalid, Noraini M., et al., Purification and Partial Characterization of a Prolyl-Dipeptidyl Aminopeptidase From *Lactobacillus helveticus* CNRZ 32, Applied and Environmental Microbiology (1990), pp. 381-388.

Kieffer, Timothy J. et al., Degradation of Glucose-Dependant Insulinotropic Polypeptide and Truncated Glucagon-Like Peptide 1 in Vitro and in Vivo by Dipeptidyl Peptidase IV, Endocrinology, vol. 136, No. 8 (1995) 3585-3596.

Kim, H.O. et al., Structure-Activity Relationships of 1,3-Dialkylxanthine Derivatives at Rat $A_3$ Adenosine Receptors, Journal of Medicinal Chemistry, vol. 37, 1994, pp. 3373-3382, XP002329848.

Kimura, Toshikiro et al., Oral Administration of Insulin as Poly(Vinyl Alcohol)-Gel Spheres in Diabetic Rats, Biological & Pharmaceutical Bulletin, vol. 19, No. 6 (1996), 897-900.

Kobe, J. et al.: "The synthesis of s-triazolo[4.3-a]1,3,5-triazines" Tetrahedron, Elsevier Science Publishers, Amsterdam, NL, vol. 26, Jul. 1970, pp. 3357-3368, XP002390908.

Koreeda, Yuji et al., Isolation and Characterization of Dipeptidyl Peptidase IV From *Prevotella loescheii* ATCC 15930, Archives of Oral Biology, 46 (2001), 759-766.

Kotra, L. P. et al.: "4-Azido-2-pyrimidone Nucleosides and Related Chemistry" Journal of Organic Chemistry, American Chemical Society, Easton, US, vol. 62, 1997, pp. 7267-7271, XP002390905.

Kozhevnikov et al. Tr. Perm. Sel.-Khoz. Inst. (1971), No. 79, 66-72 From ref. Zh., Khim. 1972, Abstr. No. 9Zh404 Journal (English Abstract attached).

Kusar, Mihael et al., Diethyl N,N-Dimethylaminomethylenemalonate in the Synthesis of Fused Heterocyclic Systems, Heterocyclic Chem. 33 (1996) pp. 1041-1046.

Abstract of Lakhan et al. Journal of Indian Chemical Society (1987), 64 (5), 316-18 (2 pages).

Li Jinping, et al., Permolybdate and Pertungstate—Potent Stimulators of Insulin Effects in Rat Adipocytes: Mechanism of Action, Biochemistry, 34 (1995) 6218-6225.

Lin, Jian, Total Synthesis and Biological Evaluation of Fluoroolefin-containing Dipeptidyl Isosteres as Inhibitors of Dipeptidyl Peptidase IV (CD26), Dissertation presented to State University of New York at Albany, Department of Chemistry (1998).

Loeser, Eric et al., Selective N-Alkylation of Primary Amines with Chloroacetamides Under pH-Controlled Aqueous Conditions, Synthetic Communications, 32(3) (2002) pp. 403-409.

Majim R. Berichet der Deutschen Chemischen Gesellschaft 1908 41 pp. 176-186.

Mall et al. Reactivity Difference of Cis-Trans Pairs: Differnt Behavior of Stillbene Oxides and Activates Stibene Imines, 1987, Journal of Organic Chemistry, 1987, vol. 52, pp. 4812-4814.

Marcus et al. PubMed Abstract (Intervirology, 45/4-6):260-6) 2002.

Mannucci, Eduardo, et al., Effect of Metaformin on Glucagon-Like Peptide-1 (GLP-1) and Leptin Levels in Obese Nondiabetic Subjects, Diabetes Care, vol. 24, No. 3 (2001) 489-494.

Mentlein, Rolf et al., Dipeptidyl-Peptidase IV Hydrolyses gastric Inhibitory Polypeptide, Glucagon-Like Peptide-1(7-36)amide, Peptide Histidine Methionine and is Respoinsible for Their Degradation in Human Serum, Eur. J. Biochem, vol. 214, 829-835 (1991).

Molina, P. et al.: "Iminophosphorane-mediated annulation of 1,3,5-triazine to benzimidazole: Synthesis of 1,3,5-triazino[1,2-a]benzimidazoles" Synthesis 1992 Germany, No. 3, 1992- pp. 297-302, XP002390907.

Mukerjee, S.S. et al., Chronic Toxicity Studies of a Hypoglycemic Compound: Centpiperalone in Rats & Rhesus Monkeys, Indian Journal of Experimental Biology, vol. 17 (1979) pp. 1346-1349.

Mukerjee, S.S. et al., Effect of 2-piperazino-4(3H)-quinazolinone monoacetate on the tissue respiration, glucose uptake and lactic acid production by rat hemidiaphragm, Biochemical Pharmacology, vol. 23 (1974) 3066-3067.

Mukerjee, S.S. et al., Studies on the Mechanism of Centpiperalone-Induced Hypoglycemia, Acta Diabet. Lat 13, 8 (1976) p. 8.

Mukerjee, S.S. et al., Tissue Distribution of [$^3$H]Centpiperalone after Oral Administration, Indian J. Biochem. Biophys., vol. 17 (1980) pp. 399-401.

Mukherjee, S.S. et al., A novel hypoglycemic compound, Biochemical Pharmacology, vol. 22 (1972) pp. 1529-1531.

Mukherjee, Surath K. et al., Effect of 2-piperazino-4(3H)-quinazolinone monoacetate on some aspects of carbohydrate metabolism of albino rats, Biochemical Pharmacology, vol. 22 (1973) pp. 2205-2206.

Mukherjee, Surath K. et al., Influence of Timing Oral Dosing of a Novel Hypoglycaemic Agent A-4166 in Relation to Food, Diabetologia vol. 38 A194 Supplement 1 (1995).

Mukherjee, Surath K. et al., Studies on the Metabolic Changes Induced by a Synthetic Insulinogenic Agent, Ind. J. Physiol. & Allied Sci., vol. 30, No. 3 (1976) pp. 105-116.

Murthy, G. Rama et al., New Hypoglycemic Agents: Part V—Synthesis & Hypoglycemic Activity of Some New 1-[[p-(4-OXO-2-Methyl/Phenyl-3 (4H)-Quinazolinyl) Phenyl]] 3-Aryl-2-Ureas, Indian Drugs, 25 (1) (1987) pp. 19-22.

Murthy, G. Rama et al., New Hypoglycemic Agents: Synthesis and Hypogylcemic Activity of Some New 1-[{p-(4-OXO-2-Substituted-3(4H)-Quinazolinyl)-Phenyl} Sulphonyl]-3-Aryl/Cyclohexyl-2-Thioureas, Current Science, vol. 56, No. 24 (1987) pp. 1263-1265.

Nakamura, Seiji, et al., Effect of Chronic Vanadate Administration in Partially Depancreatized Rats, Diabetes Research and Clinical Practice 27 (1995) pp. 51-59. (Abstract Only).

Ohkubo, I., et al., Dipeptidyl Peptidase IV From Porcine Seminal Plasma: Purification, Characterization, and N-Terminal Amino Acid Sequence, J. Biochem. (Tokyo) (1994) 116(5) pp. 1182-11826.

Pandeya, S.N. et al., Synthesis of Some New Amidine Derivatives As Potent Hypoglycemic Agents, Pharmacological Research Communications, vol. 17, No. 8 (1985) pp. 699-709.

Patent Asbstracts of Japan Publication No. 2002338551, Publication Date Nov. 27, 2002.

Pattanaik et al. Indian Journal of Chemistry, Section B; Organic Chemistry including Medicinal Chemistry (1998), 37B (12), 1304-1306 from STN CAS online search printout (3 pages).

Patent Abstracts of Japan, vol. 2003, No. 12, Xanthine Derivative, Dec. 5, 2003 & JP 2003 300977 A (Sumitomo Pharmaceut Co Ltd), Oct. 21, 2003, Abstract.

Pauly, R.P. et al., Inhibition of Dipeptydyl Peptidase IV (DPIV) in Rat Results in Improved Glucose Tolerance, Regulatory Peptides vol. 64, Issues 1-3 (1996) p. 148.

Ram, Vishnu Ji et al., Synthesis and Antihyperglycemic Activity of Suitably Functionalized 3H-quinazolin-4-ones, Bioorganic & Medicinal Chemistry 11 (2003), pp. 2439-2444.

Rauchman, B.S. et al. "2,4—Diamino-5-benylpyrimidines and Analogues as antibacterial Agents", Journal of Med. Chem., vol. 23, 1980, pp. 384-391, XP002335048 Scheme II.

Sammour et al. Egyptian Journal of Chemistry (1979) vol. Date 1976, 19(6), 1109-16. (Abstract 2 pages).

Sawyer, James H. et al., Pyrido[1,2-a]pyrimidinium Salts. Part 1. Synthesis from 2-Aminopyridines and Interconversion with 2-(2-Acylvinylamino) pyridines, J.C.S. Perkin I (1972), 1138-1143.

Saxena, A.M. et al., Mode of action of three structurally different hypoglycemic agents: A comparative study, Indian Journal of Experimental Biology, vol. 34 (1996), pp. 351-355.

Sedo, Aleksi et al., Dipeptidyl peptidase IV-like molecules: homologous proteins or homologous activities? Biochimica et Biophysica Acta 1550 (2001), pp. 107-116.

Sekiya, T. et al., Pyrimidine derivatives. III (1) Synthesis of hypoglycemic 4-alkoxy-2-piperazino-activity of 6-polymethylenepyrmidines, Eur. J. Med. Chem. (1982), 75-79.

Senten, Kristel et al., Development of Potent and Selective Dipeptidyl Peptidase II Inhibitors, Bioorganic & Medicinal Chemistry Letters 12 (2002) pp. 2825-2828.

Seth, M. et al., Syntheses of 2-Substituted & 2,3-Distributed 4(3H)-Quinazolones, Indian Journal of Chemistry, vol. 14B (1975), 536-540.

Sharma, Arun K., et al. Tandem sigmatropic shifts in [4 +2] cycloaddition reactions of 1,3-diazabuta-1,3-dienes with butadienylketene: synthesis of pyrimidinone derivatives. J. Chem. Soc., Perkin Trans. 1, 2002, 774-784.

Shimazawa, Rumiko et al., Novel Small Molecule Nonpeptide Aminopeptidase N Inhibitors with a Cyclic Imide Skeleton, J. Enzyme Inhibition, vol. 14 (1999) pp. 259-275.

Shisheva, Assia, et al., Insulinlike Effects of Zinc Ion in Vitro and in Vivo; Preferential Effects on Desensitized Adipocytes and Induction of Normoglycemia in Streptozocin-Induced Rats, Diabetes, vol. 41 (1992), pp. 982-988.

Abstract of Shyam et al. Current Science (1975), 44(16), 572-4 (one page).

Sinyak, R. S. et al., Synthesis and Biological Properties of Derivatives of 4-Heterylmercaptoquinazoline, Translated from Khimiko-farmatsevticheskii Zhurnal, vol. 20, No. 2, pp. 168-171 (1986), pp. 103-105.

Snider et al. 1994:435089 HCAPLUS No. 121:35089 Tetrahedron Ltrs (1994), 35(4), 531-4.

Snider, B. et al. HCAPLUS Doc No. 122:132810 Journal Organic Chem (1994), 59(26), 8065-70.

Sokal, Joseph E., Basal Plasma Glucagon Levels of Man, Journal of Clinical Investigation, vol. 46, No. 5 (1967) pp. 778-785.

Soliman et al. Journal of the Chemical Society of Pakistan (1986), 8(2), 97-106. (Abstract 2 pages).

Somasekhara et al. Indian Journal of Pharmacey (1972), 34(5), 121-2.

Srivastava, P.P. et al., Efficacy of Centpiperalone in Combination With Biguanide & Sulfonylurea, Indian Journal of Experimental Biology, vol. 21 (1983), pp. 390-392.

Sun et al. CAPLUS Abstract 128:257413 (1998).

Tam, S. Y-K, et al.: "Nucleosides 112. Synthesis of Some New Pyrazolo-1 5-A-1 3 5-Triazines and Their C Nucleosides" Journal of Organic Chemistry, vol. 44, No. 25, 1979, pp. 4547-4553, XP002390906.

Tanaka, Keiji et al, Vanadate Inhibits the ATP-Dependant Degradation of Proteins in Reticulocytes Without Affecting Ubiquitin Conjugation, The Journal of Biological Chemistry, vol. 259, No. 4 (1983), 2803-2809.

Van Heeswijk et al., PubMed Abstract (Antivir Ther. 6(4);2001-29) Dec 2001.

Villhauer, Edwin B. et al., 1-[[(3-Hydroxy-1-adannantyl)amino]acetyl]-2-cyano-(S)-pyrrolidine: A Potent, Selective, and Orally Bioavailable Dipeptidyl Peptidase IV Inhibitor with Antihyperglycemic Properties, J. Med. Chem. 46 (2003), pp. 2774-2789.

Villhauer, Edwin B. et al., DPP-IV Inhibition and Therapeutic Potential, Annual Reports in Chemistry 36 (2001), 191-200.

Vippagunta et al, Advanced Drug Delivery Reviews 48: 3-26, 2001.

Abstract of Tiwari et al. Indian of Journal of Pharmaceutical Sciences (1978), 40(2), 40-3 (2 pages).

Wang, F. et al.: "A novel Synthesis of Aryl[1,2-a]pyrazine Derivatives" Molecules, Molecular Diversity Preservation International, Basel, CH, vol. 9, May 2004, pp. 574-582, XP002390904.

Weber, A.E.: Dipeptidyl Peptidase IV Inhibitors for the Treatment of Diabetes, Journal of Medicinal Chemistry, vol. 47, 2004 pp. 4135-4141, XP002329845.

West, Antony R., Solid State Chemistry and its Applictions, Wile, New York, 1988, pp. 358 & 365.

Wolf et al., CAPLUS Abstract 115: 114452 (1991).

Wolf Manfred E. "Burger's Medicinal Chemistry, 5ed, Part 1" John Wiley and Sons, 1995, pp. 975-977.

XP002310117 Database Crossfire Beilstein Institut Zur Foerderung Der Chmischen Wissenschaften. XP002310117. Beilstein Registry No. 8373244 & KHIM. Geterotsikl. Soedin., No. 8, 1998, pp. 1125-1129.

XP002310118 Database Crossfire Beilstein Institut Zur Foerderung Der Chmischen Wissenschaften. XP002310118. Beilstein Registry No. 7643826 & KHIM. Geterotsikl. Soedin., vol. 32, No. 5, 1996, pp. 703-707.

XP002310119 Database Crossfire Beilstein Institut Zur Foerderung Der Chmischen Wissenschaften. XP002310119. Beilstein Registry No. 649497 & J. Pharm. Sci. vol. 80, No. 7, 1991, pp. 705-706.

XP002310120 Database Crossfire Beilstein Institut Zur Foerderung Der Chmischen Wissenschaften. XP002310120. Beilstein Registry No. 638238 & Synthetic Procedures in Nucleic Acid Chemistry, vol. 1, 1968, p. 92.

XP002310121 Database Crossfire Beilstein Institut Zur Foerderung Der Chmischen Wissenschaften. XP002310121. Beilstein Registry No. 7289032 & Nucleosides Nucleotides, vol. 14, No. 3-5, 1995, pp. 653-656.

XP002311761 Database CA Online Chemical Abstracts Service, Columbus, OH, US; Troschuetz, Reinhard et al., The reaction of O-functional benzylmalononitriles with N-bisnucleophiles as well as alcoholates. XP002311761 retrieved from STN Database accession No. 1994:217538 abstract & Archie Der Pharmazie (Winheim, Germany), 326(11), 865-9 Coden: ARPMAS; ISSN: 0365-6233, 1993.

XP002335063 Database Crossfire Beilstein Institut zur Foerderung der Wissenschaften, Franfurt am Main, DE: XP002335063. Database-Accession No. 1525341 & J. Heterocycl.Chem., vol. 12, 1975, pp. 683-687.

XP002335064 Database Crossfire Beilstein Institut zur Foerderung der Wissenchaften, Frankfurt am Main, DE; XP002335064. Database Accession No. 1447881 & J. Heterocycl.Chem., vol. 305,1972, pp. 724-730.

XP002335065 Database Crossfire Beilstein Institut zur Foerderung der Wissenchaften, Frankfurt am Main, DE; XP002335065. Database Accession No. 1447134 & J.Org.Chem., vol. 43, 1978, pp. 4069-4074.

XP002335066 Database Crossfire Beilstein Institut zur Foerderung der Wissenchaften, Frankfurt am Main, DE; XP002335066. Database Accession No. 386682 & J.Chem.Soc., 1952, pp. 4985-4990.

XP002335067 Database Crossfire Beilstein Institut zur Foerderung der Wissenchaften, Frankfurt am Main, DE; XP002335067. Database Accession No. 389575 & Chem.Ber., vol. 88, 1968, pp. 106-109.

XP002335068 Database Crossfire Beilstein Institut zur Foerderung der Wissenchaften, Frankfurt am Main, DE; XP002335068. Database Accession No. 472441 & Yakugaku Zasshi, vol. 88, 1968, pp. 106-109.

XP002335069 Database Crossfire Beilstein Institut zur Foerderung der Wissenchaften, Frankfurt am Main, DE; XP002335069. Database Accession No. 1447840 & Chem.Ber., vol. 101, No. 8, 1968, pp. 2679-2689.

XP002335070 Database Crossfire Beilstein Institut zur Foerderung der Wissenchaften, Frankfurt am Main, DE; XP002335070. Database Accession No. 1448669 & Chem.Ber., vol. 101, No. 8, 1968, pp. 2679-2689.

XP002335071 Database Crossfire Beilstein Institut zur Foerderung der Wissenchaften, Frankfurt am Main, DE; XP002335071. Database Accession No. 4991064, J.Chem.Soc.Perkin Trans.1, 1980, pp. 1370-1380.

XP002335072 Database Crossfire Beilstein Institut zur Foerderung der Wissenchaften, Frankfurt am Main, DE; XP002335072. Database Accession No. 990008, J.Prakt.Chem., vol. 315, 1973, pp. 1166-1168.

XP002335073 Database Crossfire Beilstein Institut zur Foerderung der Wissenchaften, Frankfurt am Main, DE; XP002335073. Database Accession No. 6219070, J.Prakt.Chem., vol. 330, No. 2, 1988, pp. 323-324.

XP002335074 Database Crossfire Beilstein Institut zur Foerderung der Wissenchaften, Frankfurt am Main, DE; XP002335074. Database Accession No. 392446, J.Heterocycl.Chem., vol. 8, 1971, pp. 367-371.

XP002335075 Database Crossfire Beilstein Institut zur Foerderung der Wissenchaften, Frankfurt am Main, DE; XP002335075. Database Accession No. 4742608, J. Prakt.Chem., vol. 333, No. 1, 1991, pp. 149-151.

XP002335076 P002335076 Database Crossfire Beilstein Institut zur Foerderung der Wissenchaften, Frankfurt am Main, DEe; XP002335076. Database Accession No. 490809, & Angew.Chem., vol. 84, 1972, p. 1185.

XP002392081 Database Biosis [Online] Biosciences Information Service, Philadelphia, PA, US; 1991, Bahaji E-H et al.: "Studies on Immunostimulating Derivatives Synthesis of Some Pyrrolo-1 2-C-Pyrimidines" XP002392081. Database accession no. PREV199192140000 abstract.

XP002392082 Database Beilstein [online] Beilstein Crossfire Institut Zur Forderung Der Chemischen Wissenschaften, DE; 1991, XP002392082. Database Accession No. BRN 5340228 abstract.

XP00239083 Database Beilstein [online] Beilstein Crossfire Institut Zur Forderung Der Chemischen Wissenschaften, DE; Citation No. 5593678 1991, XP00239083.

XP002392084 Database Ca [online] Chemical Abstract service, Columbus, Ohio, US; Reg No. 102482-94-0 Liu, Gang: "Fungal endophyte-epichloe and its secondary metabolites" XP002392084. Database Accession No. 2004:340837 abstract.

XP002392085 Database Beilstein [online] Beilstein Crossfire Institut Zur Foerderung Der Chemischen Wissenschaften, DE; 1924, XP002392085. Database Accession No. BRN 3799088 abstract.

XP002392086 Database Beilstein [online] Beilstein Corssfire Institut Zur Foerderung Der Chemischen Wissenschaften, DE; 1989 XP002392086. Database Accession No. BRN 5951213 abstract.

XP002392087 Database Beilstein [online] Beilstein Crossfire Institut Zur Foerderung Der Chemischen Wissenschaften, DE; 1960 XP002392087. Database Accession No. BRN 609897 abstract.

XP002392088 Database Beilstein [online] Beilstein Crossfire Institut Zur Foerderung Der Chemischen Wissenschaften, DE; 1993 XP002392088. Database Accession No. BRN 6139401 abstract.

XP002392089 Database Beilstein [online] Beilstein Crossfire Institut Zur Foererung Der Chemischen Wissenschaften DE; 1974 XP002392089. Database Accession No. BRN 514343 abstract.

* cited by examiner

METHODS OF MAKING POLYMORPHS OF BENZOATE SALT OF 2-[[6-[(3R)-3-AMINO-1-PIPERIDINYL]-3,4-IHYDRO-3-METHYL-2,4-DIOXO-1(2H)- PYRIMIDINYL] METHYL]-BENZONITRILE

RELATED APPLICATION

This application is a continuation of U.S. Utility application Ser. No. 11/531,595, filed Sep. 13, 2006, which claims benefit of U.S. Provisional Application No. 60/718,133 filed Sep. 16, 2005, all of which is incorporated herein by reference.

FIELD OF THE INVENTION

The present invention relates generally to polymorphs of the benzoate salt of 2-[[6-[(3R)-3-amino-1-piperidinyl]-3,4-dihydro-3-methyl-2,4-dioxo-1(2H)-pyrimidinyl]methyl]-benzonitrile (referred to herein as "Compound I"); compositions, kits and articles of manufacture comprising polymorphs of Compound I; and methods of their use.

DESCRIPTION OF RELATED ART

Dipeptidyl Peptidase IV (IUBMB Enzyme Nomenclature EC.3.4.14.5) is a type II membrane protein that has been referred to in the literature by a wide a variety of names including DPP4, DP4, DAP-IV, FAPβ adenosine deaminase complexing protein 2, adenosine deaminase binding protein (ADAbp), dipeptidyl aminopeptidase IV; Xaa-Pro-dipeptidyl-aminopeptidase; Gly-Pro naphthylamidase; postproline dipeptidyl aminopeptidase IV; lymphocyte antigen CD26; glycoprotein GP110; dipeptidyl peptidase IV; glycylproline aminopeptidase; glycylproline aminopeptidase; X-prolyl dipeptidyl aminopeptidase; pep X; leukocyte antigen CD26; glycylprolyl dipeptidylaminopeptidase; dipeptidyl-peptide hydrolase; glycylprolyl aminopeptidase; dipeptidyl-aminopeptidase IV; DPP IV/CD26; amino acyl-prolyl dipeptidyl aminopeptidase; T cell triggering molecule Tp103; X-PDAP. Dipeptidyl Peptidase IV is referred to herein as "DPP-IV".

DPP-IV is a non-classical serine aminodipeptidase that removes Xaa-Pro dipeptides from the amino terminus (N-terminus) of polypeptides and proteins. DPP-IV dependent slow release of dipeptides of the type X-Gly or X-Ser has also been reported for some naturally occurring peptides.

DPP-IV is constitutively expressed on epithelial and endothelial cells of a variety of different tissues (intestine, liver, lung, kidney and placenta), and is also found in body fluids. DPP-IV is also expressed on circulating T-lymphocytes and has been shown to be synonymous with the cell-surface antigen, CD-26. DPP-IV has been implicated in a number of disease states, some of which are discussed below.

DPP-IV is responsible for the metabolic cleavage of certain endogenous peptides (GLP-1 (7-36), glucagon) in vivo and has demonstrated proteolytic activity against a variety of other peptides (GHRH, NPY, GLP-2, VIP) in vitro.

GLP-1 (7-36) is a 29 amino-acid peptide derived by post-translational processing of proglucagon in the small intestine. GLP-1 (7-36) has multiple actions in vivo including the stimulation of insulin secretion, inhibition of glucagon secretion, the promotion of satiety, and the slowing of gastric emptying. Based on its physiological profile, the actions of GLP-1 (7-36) are believed to be beneficial in the prevention and treatment of type II diabetes and potentially obesity. For example, exogenous administration of GLP-1 (7-36) (continuous infusion) in diabetic patients has been found to be efficacious in this patient population. Unfortunately, GLP-1 (7-36) is degraded rapidly in vivo and has been shown to have a short half-life in vivo ($t_{1/2}$=1.5 minutes).

Based on a study of genetically bred DPP-IV knock out mice and on in vivo/in vitro studies with selective DPP-IV inhibitors, DPP-IV has been shown to be the primary degrading enzyme of GLP-1 (7-36) in vivo. GLP-1 (7-36) is degraded by DPP-IV efficiently to GLP-1 (9-36), which has been speculated to act as a physiological antagonist to GLP-1 (7-36). Inhibiting DPP-IV in vivo is therefore believed to be useful for potentiating endogenous levels of GLP-1 (7-36) and attenuating the formation of its antagonist GLP-1 (9-36). Thus, DPP-IV inhibitors are believed to be useful agents for the prevention, delay of progression, and/or treatment of conditions mediated by DPP-IV, in particular diabetes and more particularly, type 2 diabetes mellitus, diabetic dislipidemia, conditions of impaired glucose tolerance (IGT), conditions of impaired fasting plasma glucose (IFG), metabolic acidosis, ketosis, appetite regulation and obesity.

DPP-IV expression is increased in T-cells upon mitogenic or antigenic stimulation (Mattem, T., et al., *Scand. J. Immunol.*, 1991, 33, 737). It has been reported that inhibitors of DPP-IV and antibodies to DPP-IV suppress the proliferation of mitogen-stimulated and antigen-stimulated T-cells in a dose-dependant manner (Schon, E., et al., *Biol. Chem.*, 1991, 372, 305). Various other functions of T-lymphocytes such as cytokine production, IL-2 mediated cell proliferation and B-cell helper activity have been shown to be dependent on DPP-IV activity (Schon, E., et al., *Scand. J. Immunol*, 1989, 29, 127). DPP-IV inhibitors, based on boroProline, (Flentke, G. R., et al., *Proc. Nat. Acad. Sci. USA*, 1991, 88, 1556) although unstable, were effective at inhibiting antigen-induced lymphocyte proliferation and IL-2 production in murine CD4+ T-helper cells. Such boronic acid inhibitors have been shown to have an effect in vivo in mice causing suppression of antibody production induced by immune challenge (Kubota, T. et al., *Clin. Exp. Immun.*, 1992, 89, 192). The role of DPP-IV in regulating T lymphocyte activation may also be attributed, in part, to its cell-surface association with the transmembrane phosphatase, CD45. DPP-IV inhibitors or non-active site ligands may possibly disrupt the CD45-DPP-IV association. CD45 is known to be an integral component of the T-cell signaling apparatus. It has been reported that DPP-IV is essential for the penetration and infectivity of HIV-1 and HIV-2 viruses in CD4+ T-cells (Wakselman, M., Nguyen, C., Mazaleyrat, J.-P., Callebaut, C., Krust, B., Hovanessian, A. G., Inhibition of HIV-1 infection of CD 26+ but not CD 26-cells by a potent cyclopeptidic inhibitor of the DPP-IV activity of CD 26. Abstract P.44 of the 24th European Peptide Symposium 1996). Additionally, DPP-IV has been shown to associate with the enzyme adenosine deaminase (ADA) on the surface of T-cells (Kameoka, J., et al., *Science*, 193, 26 466). ADA deficiency causes severe combined immunodeficiency disease (SCID) in humans. This ADA-CD26 interaction may provide clues to the pathophysiology of SCID. It follows that inhibitors of DPP-IV may be useful immunosuppressants (or cytokine release suppressant drugs) for the treatment of among other things: organ transplant rejection; autoimmune diseases such as inflammatory bowel disease, multiple sclerosis and rheumatoid arthritis; and the treatment of AIDS.

It has been shown that lung endothelial cell DPP-IV is an adhesion molecule for lung-metastatic rat breast and prostate carcinoma cells (Johnson, R. C., et al., *J. Cell Biol.*, 1993, 121, 1423). DPP-IV is known to bind to fibronectin and some metastatic tumor cells are known to carry large amounts of fibronectin on their surface. Potent DPP-IV inhibitors may be useful as drugs to prevent metastases of, for example, breast and prostrate tumors to the lungs.

High levels of DPP-IV expression have also been found in human skin fibroblast cells from patients with psoriasis, rheumatoid arthritis (RA) and lichen planus (Raynaud, F., et al., *J. Cell Physiol.*, 1992, 151, 378). Therefore, DPP-IV inhibitors may be useful as agents to treat dermatological diseases such as psoriasis and lichen planus.

High DPP-IV activity has been found in tissue homogenates from patients with benign prostate hypertrophy and in prostatosomes. These are prostate derived organelles important for the enhancement of sperm forward motility (Vanhoof, G., et al., *Eur. J. Clin. Chem. Clin. Biochem.*, 1992, 30, 333). DPP-IV inhibitors may also act to suppress sperm motility and therefore act as a male contraceptive agent. Conversely, DPP-IV inhibitors have been implicated as novel for treatment of infertility, and particularly human female infertility due to Polycystic ovary syndrome (PCOS, Stein-Leventhal syndrome) which is a condition characterized by thickening of the ovarian capsule and formation of multiple follicular cysts. It results in infertility and amenorrhea.

DPP-IV is thought to play a role in the cleavage of various cytokines (stimulating hematopoietic cells), growth factors and neuropeptides.

Stimulated hematopoietic cells are useful for the treatment of disorders that are characterized by a reduced number of hematopoietic cells or their precursors in vivo. Such conditions occur frequently in patients who are immunosuppressed, for example, as a consequence of chemotherapy and/or radiation therapy for cancer. It was discovered that inhibitors of dipeptidyl peptidase type IV are useful for stimulating the growth and differentiation of hematopoietic cells in the absence of exogenously added cytokines or other growth factors or stromal cells. This discovery contradicts the dogma in the field of hematopoietic cell stimulation, which provides that the addition of cytokines or cells that produce cytokines (stromal cells) is an essential element for maintaining and stimulating the growth and differentiation of hematopoietic cells in culture. (See, e.g., PCT Intl. Application No. PCT/US93/017173 published as WO 94/03055).

DPP-IV in human plasma has been shown to cleave N-terminal Tyr-Ala from growth hormone-releasing factor and cause inactivation of this hormone. Therefore, inhibitors of DPP-IV may be useful in the treatment of short stature due to growth hormone deficiency (Dwarfism) and for promoting GH-dependent tissue growth or re-growth.

DPP-IV can also cleave neuropeptides and has been shown to modulate the activity of neuroactive peptides substance P, neuropeptide Y and CLIP (Mentlein, R., Dahms, P., Grandt, D., Kruger, R., Proteolytic processing of neuropeptide Y and peptide YY by dipeptidyl peptidase IV, *Regul. Pept.*, 49, 133, 1993; Wetzel, W., Wagner, T., Vogel, D., Demuth, H.-U., Balschun, D., Effects of the CLIP fragment ACTH 20-24 on the duration of REM sleep episodes, *Neuropeptides*, 31, 41, 1997). Thus DPP-IV inhibitors may also be useful agents for the regulation or normalization of neurological disorders.

A need still exists for DPP-IV inhibitors that have advantageous potency, stability, selectivity, toxicity and/or pharmacodynamics properties and which thus may be used effectively in pharmaceutical compositions to treat disease states by the inhibition of DPP-IV.

SUMMARY OF THE INVENTION

The benzoate salt of 2-[[6-[(3R)-3-amino-1-piperidinyl]-3,4-dihydro-3-methyl-2,4-dioxo-1(2H)-pyrimidinyl]methyl]-benzonitrile (referred to herein as Compound I) which has the formula:

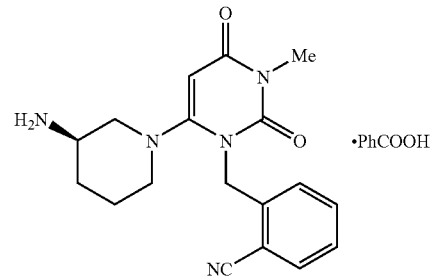

is a DPP-IV inhibitor that is described in U.S. patent application Ser. No. 11/080,992, filed Mar. 15, 2005, which is hereby incorporated herein by reference in its entirety.

The present invention provides a novel polymorph of Compound I, as well as compositions comprising one or more of the novel polymorphs. For ease of reference, the polymorphs described herein is referred to consistently as Form A and amorphous Form 1.

1. Form A

In one embodiment, the present invention relates to a polymorph of Compound I, referred to herein as Form A. Based on its physical properties, Form A is a crystalline form.

Form A may be characterized as having one or more of the following physical characteristics (it being noted that a composition need not necessarily exhibit all of these characteristics in order to indicate the presence of Form A):

(a) may be formed by crystallization from any of the following solvent systems (i) acetone; (ii) acetonitrile; (iii) butanol; (iv) dimethylsulfoxide; (v) dioxane; (vi) ethanol; (vii) ethanol and isopropyl alcohol; (viii) ethanol and water; (ix) ethyl acetate; (x) heptane; (xi) isopropanol; (xii) isopropyl acetate; (xiii) methanol; (xiv) methyl ethyl ketone; (xv) methyl isobutyl ketone; (xvi) 2,2,2-trifluoroethanol; (xvii) tetrahydrofuran; (xviii) toluene; (xix) water; and (xx) ethanol and heptane.

(b) has an X-ray powder diffraction pattern with salient features being major diffraction lines as shown below:

| °2θ | | | | | | | | | | |
|---|---|---|---|---|---|---|---|---|---|---|
| | 9.12 | 9.44 | 10.48 | 10.84 | 11.34 | 12.49 | 12.84 | 14.09 | 14.38 | 14.90 | 15.20 |
| I/I$_o$ | 7 | 56 | 3 | 28 | 10 | 8 | 3 | 7 | 5 | 10 | 27 |
| °2θ | | | | | | | | | | |
| | 16.83 | 17.48 | 17.82 | 18.75 | 20.09 | 20.48 | 20.64 | 20.92 | 21.18 | 21.52 | 21.82 |
| I/I$_o$ | 3 | 4 | 50 | 100 | 21 | 5 | 20 | 83 | 51 | 17 | 34 |

-continued

| °2θ | | | | | | | | | | |
|---|---|---|---|---|---|---|---|---|---|---|
| 22.10 | 22.88 | 23.34 | 23.64 | 23.88 | 24.22 | 24.44 | 25.87 | 26.14 | 27.02 | 27.62 |
| I/I$_o$ 14 | 9 | 11 | 20 | 9 | 7 | 12 | 16 | 4 | 28 | 16 |

| °2θ | | | | | | | | | | |
|---|---|---|---|---|---|---|---|---|---|---|
| 28.09 | 28.52 | 29.06 | 29.26 | 29.74 | 30.17 | 31.66 | 33.02 | 34.34 | 34.86 | 35.12 |
| I/I$_o$ 13 | 25 | 14 | 9 | 8 | 3 | 4 | 3 | 12 | 7 | 11 |

| °2θ | | | | | | |
|---|---|---|---|---|---|---|
| 35.50 | 36.07 | 37.32 | 37.52 | 37.82 | 38.02 | 38.29 |
| I/I$_o$ 8 | 8 | 3 | 4 | 9 | 9 | 15 | and, in particular, having the following distinguishing peaks:

| Peak Position (°2θ) | I/I$_o$ |
|---|---|
| 9.44 | 56 |
| 10.84 | 28 |
| 17.82 | 50 |
| 18.75 | 100 |
| 25.87 | 16 |
| 28.52 | 25 |

(c) has an IR spectrum comprising absorption peaks at 830, 876, 910, 950, 987, 1004, 1026, 1063, 1094, 1135, 1173, 1212, 1231, 1284, 1316, 1334, 1365, 1384, 1447, 1458, 1474, 1532, 1592, 1613, 1697, 2082, 2230, 2540, 2596, 2743, 2860, 2958, 2979 and 3085 cm$^{-1}$;

with an IR spectrum comprising unique FT-IR peak positions (peaks that show no other peak within ±4 cm$^{-1}$ to make up a unique set) at 1212, 1365, 1447, 1613 and 1697 cm$^{-1}$;

(d) has FT-Raman peak positions at 825, 881, 910, 918, 987, 1003, 1027, 1039, 1065, 1084, 1103, 1135, 1157, 1167, 1172, 1184, 1206, 1235, 1288, 1337, 1365, 1385, 1417, 1446, 1461, 1474, 1557, 1577, 1597, 1624 1652, 1689, 2230, 2860, 2883, 2957, 2970, 2983, 3026, 3053 and 3070 cm$^{-1}$;

with unique FT-Raman peak positions (peaks that show no other peaks within ±4 cm$^{-1}$ to make up a unique set) at 1065, 1103, 1235, 1288, 1337, 1365, 1624, 1689, 2883, 2983 and 3026 cm$^{-1}$;

(e) has a differential scanning calorimetry spectrum having an endotherm range of about 173° C. to about 195° C., optionally an endotherm range of about 180° C. to about 190° C., and optionally an endotherm at 186° C.;

(f) has a thermogravimetric analysis data showing a 0.2% weight loss from 26-159° C.; and/or (g) formed from the conversion of the amorphous Form 1 by stressing the amorphous Form 1 with heat, high relative humidity or organic vapors, or by wet milling of amorphous Form 1 with water.

2. Amorphous Forms 1

The amorphous Form 1 may be characterized as having one or more of the following physical characteristics (it being noted that a composition need not necessarily exhibit all of these characteristics in order to indicate the presence of the amorphous Form 1):

(a) may be formed by (i) rotoevaporation from methanol; (ii) fast evaporation from water; (iii) lyophilization from water; (iv) crystallization from ethyl acetate and hexanes; and (v) crystallization from isopropyl acetate and hexanes;

(b) has an X-ray powder diffraction pattern that shows a broad halo with no specific peaks present;

(c) has an IR spectrum comprising absorption peaks at 809, 833, 868, 948, 1024, 1068, 1084, 1119, 1134, 1172, 1228, 1286, 1375, 1440, 1541, 1599, 1652, 1703, 2136, 2225, 2571, 2861, 2949 and 3062 cm$^{-1}$;

with an IR spectrum comprising unique FT-IR peak positions (peaks that show no other peaks within ±4 cm$^{-1}$ to make up a unique set) at 809, 868, 1119, 1599 and 1703 cm$^{-1}$;

(d) has FT-Raman peak position at 805, 834, 904, 1002, 1024, 1045, 1134, 1168, 1205, 1280, 1386, 1443, 1578, 1600, 1654, 1703, 2225, 2864, 2958 and 3065 cm$^{-1}$;

with unique FT-Raman peak positions (peaks that show no other peaks within ±4 cm$^{-1}$) at 805, 1280 and 1703 cm$^{-1}$;

(e) has a differential scanning calorimetry (cyclic DSC) spectrum having a Tg=70° C. (onset), exotherm at 132° C. (maxima), and an endotherm at 183° C. (onset temperature); and/or (f) has a thermogravimetric analysis data showing a 4% weight loss from 25-151° C.

Methods by which the above referenced analyses were performed in order to identify these physical characteristics are described in the Examples.

The present invention relates to compositions comprising Compound I, wherein Compound I is present as Form A or the amorphous Form 1, as described below. It is noted that other crystalline and amorphous forms of Compound I may also be present in the composition.

In one variation, the composition comprises at least 0.25%, 0.5%, 1%, 5%, 10%, 25%, 50%, 75%, 80%, 85%, 90%, 95%, 97%, or 99% of Compound I where greater than 1%, 5%, 10%, 25%, 50%, 75%, 80%, 85%, 90%, 95%, 97% or 99% of Compound I (by weight) is present in the composition as Form A or the amorphous Form 1. The composition may optionally be a pharmaceutical composition. The pharmaceutical composition may optionally further include one or more pharmaceutical carriers.

Also provided are kits and other articles of manufacture comprising a composition that comprises Compound I, wherein Compound I is present as Form A or the amorphous Form 1. In one variation, the composition comprises at least 0.25%, 0.5%, 1%, 5%, 10%, 25%, 50%, 75%, 80%, 85%, 90%, 95%, 97%, or 99% of Compound I where greater than 1%, 5%, 10%, 25%, 50%, 75%, 80%, 85%, 90%, 95%, 97% or 99% of Compound I (by weight) is present in the composition as Form A or the amorphous Form 1. The composition in the kits and articles of manufacture may optionally be a pharmaceutical composition. The pharmaceutical composition may optionally further include one or more pharmaceutical carriers.

In regard to each of the above embodiments including a pharmaceutical composition, the pharmaceutical composition may be formulated in any manner where a portion of the compound is at least partially preserved in a given polymorphic form. Optionally, a portion of the compound is at least partially preserved in a given polymorphic form for a period of time subsequent to administration of the pharmaceutical formulation to a human.

3. Methods of Making Form A and Amorphous Forms 1

Various methods are also provided for making Form A and amorphous Form 1. Various methods are also provided for manufacturing pharmaceutical compositions, kits and other articles of manufacture comprising Form A and amorphous Form 1.

4. Methods of Using Form A and Amorphous Form 1

Methods of using a pharmaceutical composition, kit and other article of manufacture comprising Form A and/or amorphous Form 1 to treat various diseases are also provided.

In one embodiment, the present invention relates to a method of inhibiting dipeptidyl peptidases comprising administering to a subject (e.g., human body) a composition where greater than 1%, 5%, 10%, 25%, 50%, 75%, 80%, 85%, 90%, 95%, 97% or 99% of Compound I (by weight) is present in the composition as Form A or amorphous Form 1. Optionally, the composition comprises at least 0.25%, 0.5%, 1%, 5%, 10%, 25%, 50%, 75%, 80%, 85%, 90%, 95%, 97%, or 99% of Compound I.

In another embodiment, the present invention relates to a method of inhibiting dipeptidyl peptidases in a subject (e.g., human body) with Compound I by administering Compound I where greater than 1%, 5%, 10%, 25%, 50%, 75%, 80%, 85%, 90%, 95%, 97% or 99% of Compound I (by weight) is present in the composition as Form A or amorphous Form 1 when the compound is administered. Optionally, the composition comprises at least 0.25%, 0.5%, 1%, 5%, 10%, 25%, 50%, 75%, 80%, 85%, 90%, 95%, 97%, or 99% or Compound I.

In another embodiment, the present invention relates to a method of inhibiting dipeptidyl peptidases in a subject (e.g., human body) with Compound I by administering Compound I where greater than 1%, 5%, 10%, 25%, 50%, 75%, 80%, 85%, 90%, 95%, 97% or 99% of Compound I (by weight) is present in the composition as Form A or amorphous Form 1 for a period of time after the compound has been administered to a human. Optionally, the composition comprises at least 0.25%, 0.5%, 1%, 5%, 10%, 25%, 50%, 75%, 80%, 85%, 90%, 95%, 97%, or 99% of Compound I.

In still another embodiment, the present invention provides a method of treating a disease state for which dipeptidyl peptidases possesses activity that contributes to the pathology and/or symptomology of the disease state, comprising administering to a subject (e.g., human body) a composition where greater than 1%, 5%, 10%, 25%, 50%, 75%, 80%, 85%, 90%, 95%, 97% or 99% of Compound I (by weight) is present in the composition as Form A or amorphous Form 1 when administered. Optionally, the composition comprises at least 0.25%, 0.5%, 1%, 5%, 10%, 25%, 50%, 75%, 80%, 85%, 90%, 95%, 97%, or 99% of Compound I.

In still another embodiment, the present invention provides a method of treating a disease state for which dipeptidyl peptidases possesses activity that contributes to the pathology and/or symptomology of the disease state, comprising causing a composition to be present in a subject (e.g., human body) where greater than 1%, 5%, 10%, 25%, 50%, 75%, 80%, 85%, 90%, 95%, 97% or 99% of Compound I (by weight) is present in the composition as Form A or amorphous Form 1 for a period of time after the composition has been administered to a human. Optionally, the composition comprises at least 0.25%, 0.5%, 1%, 5%, 10%, 25%, 50%, 75%, 80%, 85%, 90%, 95%, 97%, or 99% of Compound I.

In another embodiment, a method is provided for preventing, delaying the of progression, and/or treating conditions mediated by DPP-IV, in particular diabetes and more particularly, type 2 diabetes mellitus, diabetic dislipidemia, conditions of impaired glucose tolerance (IGT), conditions of impaired fasting plasma glucose (IFG), metabolic acidosis, ketosis, appetite regulation and obesity.

DETAILED DESCRIPTION OF THE INVENTION

Figure 1:
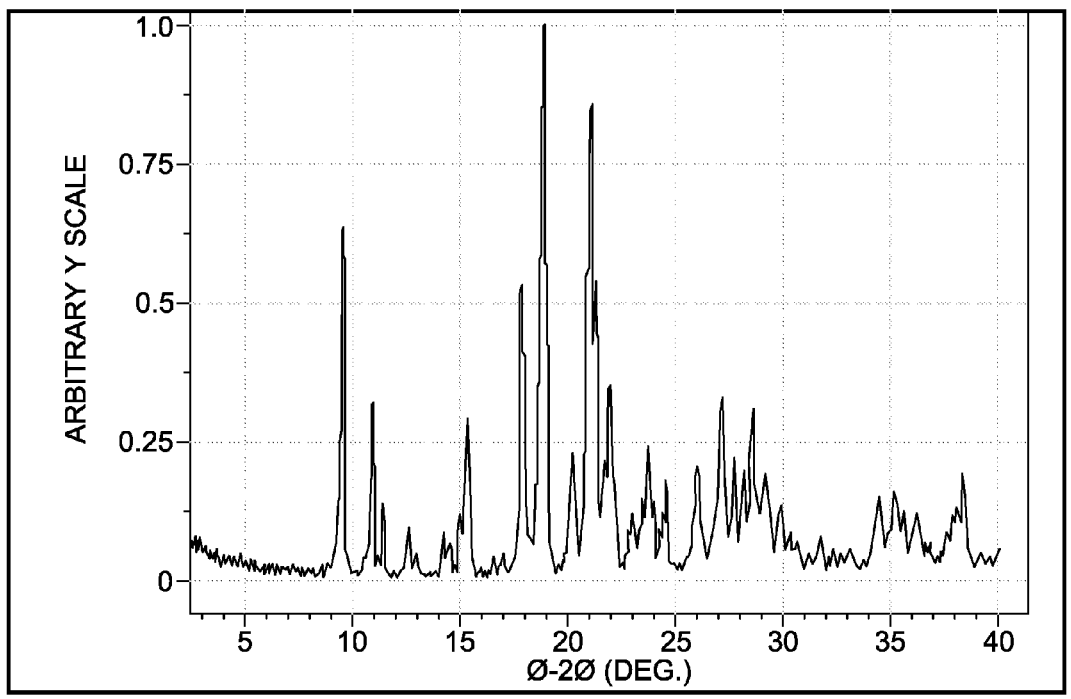
FIG. 1 illustrates the XRPD pattern of Form A, wherein the "XRPD pattern" is a plot of the intensity of diffracted lines.

The present invention provides novel polymorphs of Compound I, as well as compositions comprising Compound I where at least a portion of Compound I is present in the composition as Form A or amorphous Form 1.

Also provided are kits and other articles of manufacture with compositions comprising Compound I where at least a portion of Compound I is present in the composition as Form A or amorphous Form 1.

Various methods are also provided including methods of making the disclosed Form A and amorphous Form 1, methods for manufacturing pharmaceutical compositions comprising Compound I where at least a portion of Compound I is present in the composition as Form A and amorphous Form 1, and methods of using compositions comprising Compound I where at least a portion of Compound I is present in the composition as Form A or amorphous Form 1.

1. Preparation of Compound I

Various methods may be used to synthesize Compound I. Representative methods for synthesizing Compound I are provided in Example 1. It is noted, however, that other synthetic routes may also be used to synthesize Compound I including those disclosed in U.S. patent application Ser. No. 11/080,992, filed Mar. 15, 2005, which is hereby incorporated by reference in its entirety.

2. Preparation of Polymorphs

In general, a given polymorph of a compound may be obtained by direct crystallization of the compound or by crystallization of the compound followed by interconversion from another polymorphic form or from an amorphous state. The Examples below describe methods for testing the solubility of Compound I and methods for screening for crystallization conditions for Compound I.

Depending on the method by which a compound is crystallized, the resulting composition may contain different amounts of the compound in crystalline form as opposed to as an amorphous material. Also, the resulting composition may contain differing mixtures of different polymorphic forms of the compound.

"Crystalline", as the term is used herein, refers to a material that contains a specific compound, which may be hydrated and/or solvated, and has sufficient crystalline content to exhibit a discernable diffraction pattern by XRPD or other diffraction techniques. Often, a crystalline material that is obtained by direct crystallization of a compound dissolved in a solution or interconversion of crystals obtained under different crystallization conditions, will have crystals that contain the solvent used in the crystallization, termed a crystalline solvate. Also, the specific solvent system and physical embodiment in which the crystallization is performed, collectively termed crystallization conditions, may result in the crystalline material having physical and chemical properties that are unique to the crystallization conditions, generally due to the orientation of the chemical moieties of the compound with respect to each other within the crystal and/or the predominance of a specific polymorphic form of the compound in the crystalline material.

Depending upon the polymorphic form(s) of the compound that are present in a composition, various amounts of the compound in an amorphous solid state may also be present, either as a side product of the initial crystallization, and/or a product of degradation of the crystals comprising the crystalline material. Thus, crystalline, as the term is used herein, contemplates that the composition may include amorphous content; the presence of the crystalline material among the amorphous material being detectably among other methods by the composition having a discernable diffraction pattern.

The amorphous content of a crystalline material may be increased by grinding or pulverizing the material, which is evidenced by broadening of diffraction and other spectral lines relative to the crystalline material prior to grinding. Sufficient grinding and/or pulverizing may broaden the lines relative to the crystalline material prior to grinding to the extent that the XRPD or other crystal specific spectrum may become undiscernable, making the material substantially amorphous or quasi-amorphous.

"Amorphous", as the term is used herein, refers to a composition comprising a compound that contains too little crystalline content of the compound to yield a discernable pattern by XRPD or other diffraction techniques. Glassy materials are a type of amorphous material. Amorphous materials do not have a true crystal lattice, and are consequently glassy rather than true solids, technically resembling very viscous non-crystalline liquids. Rather than being true solids, glasses may better be described as quasi-solid amorphous material. Thus, an amorphous material refers to a quasi-solid, glassy material. Precipitation of a compound from solution, often affected by rapid evaporation of solvent, is known to favor the compound forming an amorphous solid as opposed to crystals. A compound in an amorphous state may be produced by rapidly evaporating solvent from a solvated compound, or by grinding, pulverizing or otherwise physically pressurizing or abrading the compound while in a crystalline state. General methods for precipitating and crystallizing a compound may be applied to prepare the various polymorphs described herein. These general methods are known to those skilled in the art of synthetic organic chemistry and pharmaceutical formulation, and are described, for example, by J. March, "*Advanced Organic Chemistry: Reactions, Mechanisms and Structure*," 4$^{th}$ Ed. (New York: Wiley-Interscience, 1992).

"Broad" or "broadened", as the term is used herein to describe spectral lines, including XRPD, NMR and IR spectroscopy lines, is a relative term that relates to the line width of a baseline spectrum. The baseline spectrum is often that of an unmanipulated crystalline form of a specific compound as obtained directly from a given set of physical and chemical conditions, including solvent composition and properties such as temperature and pressure. For example, broadened can be used to describe the spectral lines of a XRPD spectrum of ground or pulverized material comprising a crystalline compound relative to the material prior to grinding. In materials where the constituent molecules, ions or atoms, as solvated or hydrated, are not tumbling rapidly, line broadening is indicative of increased randomness in the orientation of the chemical moieties of the compound, thus indicative of an increased amorphous content. When comparisons are made between crystalline materials obtained via different crystallization conditions, broader spectral lines indicate that the material producing the relatively broader spectral lines has a higher level of amorphous material.

Continued grinding would be expected to increase the amorphous content and further broaden the XRPD pattern with the limit of the XRPD pattern being so broadened that it can no longer be discerned above noise. When the XRPD pattern is broadened to the limit of being indiscernible, the material may be considered to no longer be a crystalline material, and instead be wholly amorphous. For material having increased amorphous content and wholly amorphous material, no peaks should be observed that would indicate grinding produces another form.

Compositions comprising a higher percentage of crystalline content (e.g., forming crystals having fewer lattice defects and proportionately less glassy material) are generally prepared when conditions are used that favor slower crystal formation, including those slowing solvent evaporation and those affecting kinetics. Crystallization conditions may be appropriately adjusted to obtain higher quality crystalline material as necessary. Thus, for example, if poor crystals are formed under an initial set of crystallization conditions, the solvent temperature may be reduced and ambient pressure above the solution may be increased relative to the initial set of crystallization conditions in order to slow crystallization.

As one will appreciate, depending on how a composition comprising a given compound is produced and then, once produced, how the composition is stored and manipulated, will influence the crystalline content of the composition. Accordingly, it is possible for a composition to comprise no crystalline content or may comprise higher concentrations of crystalline content.

It is further noted that a compound may be present in a given composition in one or more different polymorphic forms, as well as optionally also being present as an amorphous material. This may be the result of (a) physically mixing two or more different polymorphic forms; (b) having two or more different polymorphic forms be generated from crystallization conditions; (c) having all or a portion of a given polymorphic form convert into another polymorphic form; (d) having all or a portion of a compound in an amorphous state convert into two or more polymorphic forms; as well as for a host of other reasons.

As can be seen, depending on how a composition comprising a compound is prepared, the percentage, by weight, of that compound in a given polymorphic form can vary from 0% to 100%. According to the present invention, compositions are provided where greater than 1%, 5%, 10%, 25%, 50%, 75%, 80%, 85%, 90%, 95%, 97%, or 99% or more of Compound I (by weight) is present in the composition as Form A or amorphous Form 1.

3. Polymorphs of Compound I

Described herein are Form A and amorphous Form 1 of Compound I.

Various tests may be performed in order to physically characterize the crystalline state of Compound I including but not limited to X-ray powder diffraction ("XRPD"), differential scanning calorimetry ("DSC"), thermogravimetric analysis ("TGA"), hot stage microscopy, infrared spectrometry ("IR"), Raman spectrometry and Karl Fischer analysis. The Examples below describe the methods that were used to perform the various analyses reported herein. Where possible, the results of each test for each different polymorph are provided herein.

A. Method of Making Form A of Compound I

The following describes procedures by which Form A polymorph of Compound I has been made from different samples of Compound I:

Sample No. 1924-73-02: A slurry of Compound I in acetone was filtered through 0.2 μm nylon syringe filter into a clean vial. The vial was left uncovered in a fume hood under ambient conditions for fast evaporation, yielding Form A solids after two days.

Sample No. 1924-73-08: A slurry of Compound I in methanol was filtered through 0.2 μm nylon syringe filter into a clean vial. The vial was covered with aluminum foil perforated with pinholes and placed in a fume hood for slow evaporation at ambient conditions, yielding Form A solids in two days.

Sample No. 1924-67-05: Compound I was slurried in acetonitrile on a hotplate set at 60° C. and the mixture was filtered while warm through 0.2 μm nylon syringe filter into a clean, warm vial. The vial was placed on the hotplate, which was then turned off and allowed to slowly cool to ambient temperature. Form A solids were collected by filtration after one day.

Sample No. 1994-82-01: Compound I (123 mg) was dissolved in 99:1 ethanol/isopropyl acetate (1 mL) under reflux and then was cooled to ambient temperature at a rate of 20° C./hour. Solids precipitated and the resulting slurry was agitated for 4 hours at ambient temperature. The solvent was decanted and the solids dried. The experiments yielded Form A solids.

B. Characterization of Form A of Compound I

FIG. 1 illustrates the XRPD pattern of Form A. Major diffraction lines are observed for °2θ at approximately: 9.44, 10.84, 17.82, 18.75, 25.87 and 28.52. The XRPD pattern tends to indicate that confirmed that the material is a crystalline phase, which was designated form A.

Colorless plates of Compound I were collected from ethanol-water solution. The orthorhombic cell parameters and calculated volume are: a=8.0869(2), b=9.9030(3), c=28.5471 (10) Å, V=2286.18(12) Å$^3$. For Z=4 and formula weight of 461.53 g, the calculated density is 1.34 g/cm$^3$. The quality of the structure obtained is good, as indicated by the R-value of 0.068. Usually R-values in the range of 0.02 to 0.06 are quoted for the most reliably determined structures. An ORTEP drawing of Compound I shows that the crystal structure is the same as the proposed structure. The asymmetric unit was noted to contain one free base cation and one benzoate counterion. The calculated powder pattern generated from the single crystal data with experimental XRPD patterns of Form A of Compound I are very similar, but there are small differences in °2θ position of peaks due to temperature effects. The single crystal data was collected at 150K whereas the experimental XRPD pattern was measured at ambient temperature. Differences in intensities are likely due to preferred orientation.

Figure 2:
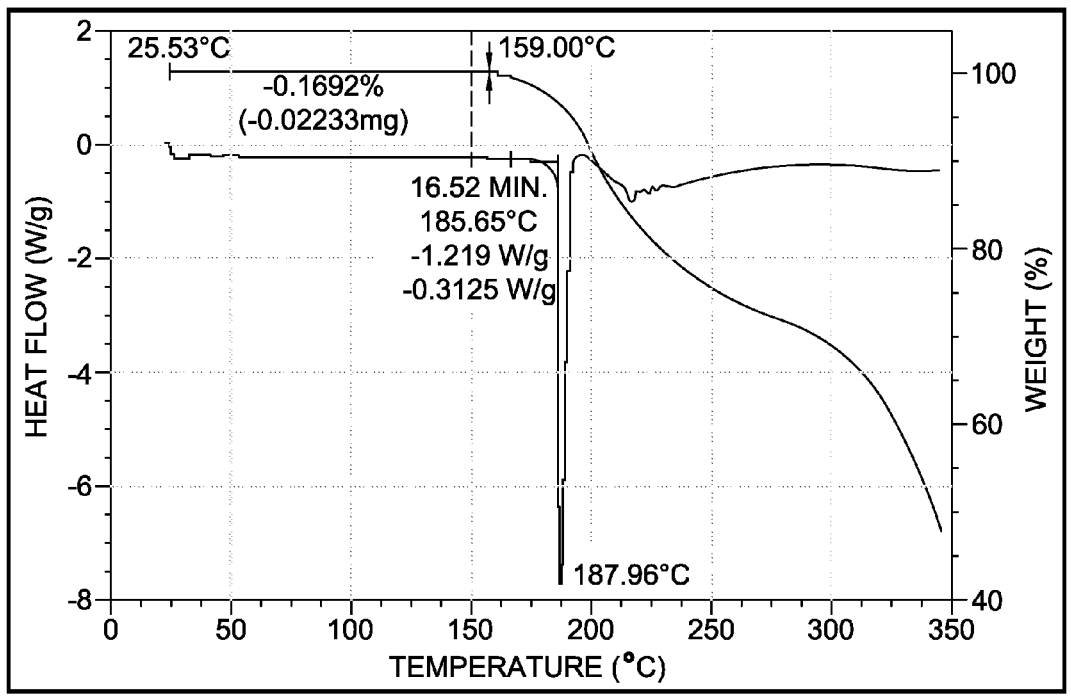
FIG. 2 is a plot of TGA data and the DSC data for Form A.

Thermogravimetric and DSC data for Form A is summarized below in Table 1A and plotted in FIG. 2. As can be seen in FIG. 2, the DSC curve exhibits several endothermic events. The endotherm maximum for the most predominant event is located near 186° C. A melting point experiment confirmed that this endothermic event is associated with the melt of the material. The series of endothermic events above the melt endotherm were not characterized further, but likely correspond to the decomposition of the sample. A broad endothermic event located below the melt endotherm for the sample can also be seen in the DSC plot for the sample of form A. This event occurs in the same temperature region as the corresponding mass loss observed in the TGA plot for a sample of form A and is consistent with the loss of volatile material from the sample.

TABLE 1A

Thermal Data for Form A

| DSC Results[1] | TGA Results[2] |
|---|---|
| Endotherm at 186° C. | 0.2% |

[1]Maximum temperature reported for transition
[2]Percent weight change from 26° C. to 159° C.

Figure 3:
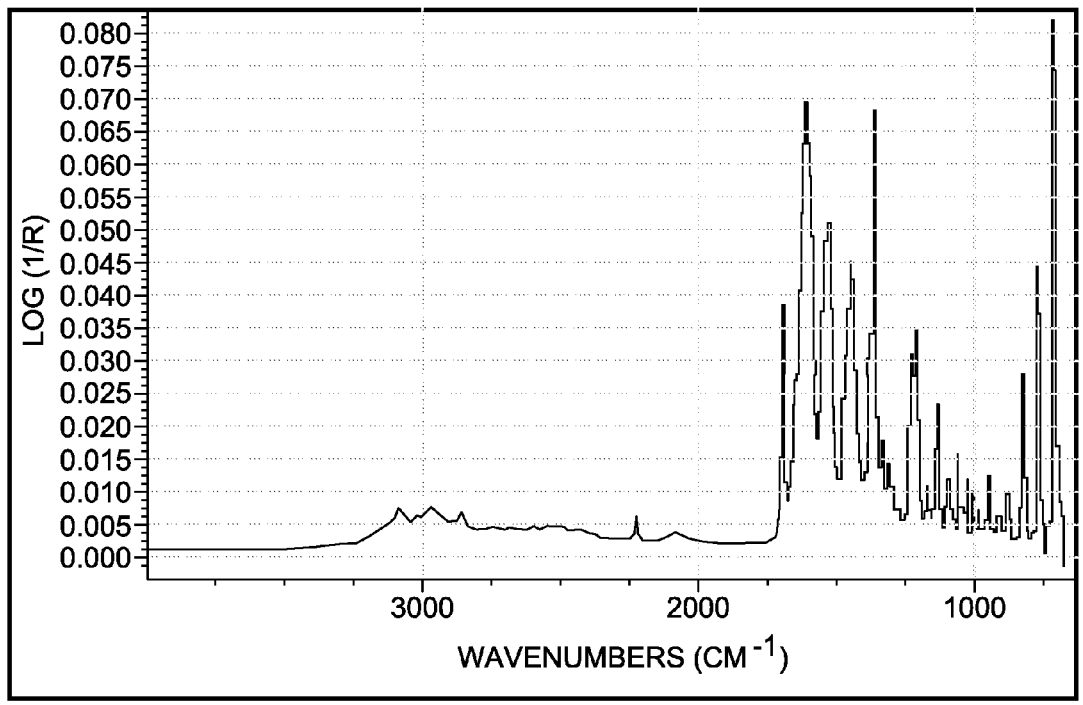
FIG. 3 is a plot of the IR absorption spectrum for Form A.

The IR spectrum for Form A (Lot no. QZ-656-17(1)) is plotted in FIG. 3.

Figure 4:
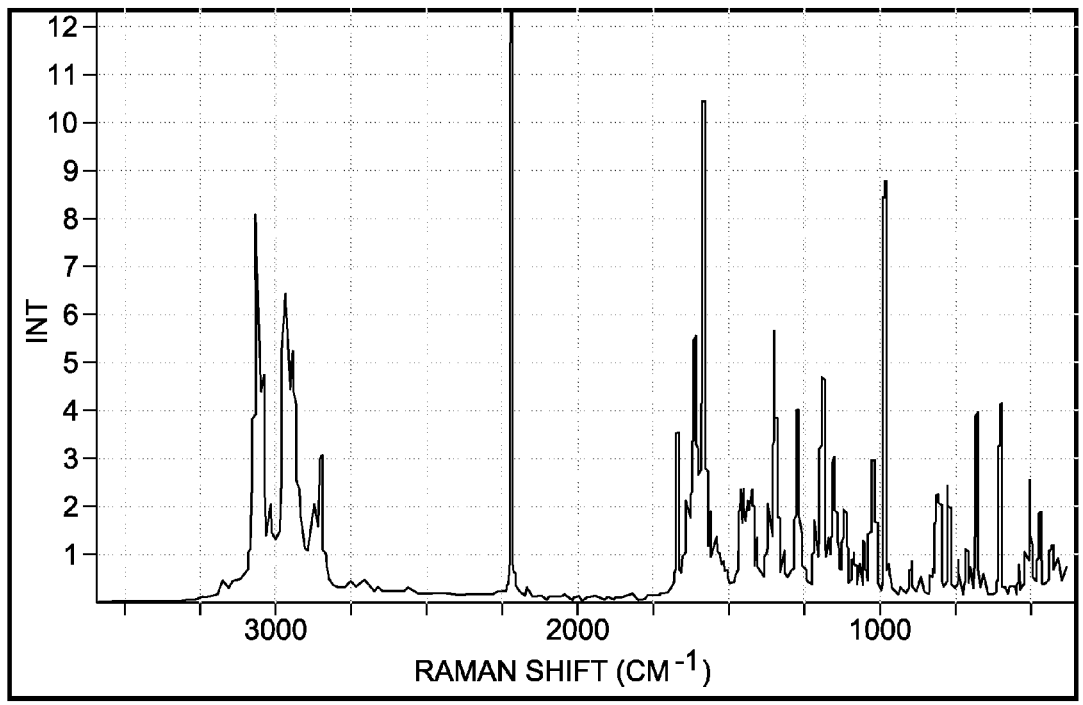
FIG. 4 is a plot of the FT-Raman absorption spectrum for Form A.

The Raman spectrum for Form A (Lot no. QZ-656-17(1)) is provided in FIG. 4.

Data regarding the moisture sorption/desorption properties of Form A are summarized in Table 2A below. The analysis showed an initial weight gain of approximately 0.035% from ambient conditions to 55% RH and a weight loss of about 0.05% between 9% and 95% RH. The desorption cycle follows a slightly different path as the sorption cycle, where the mass gained during the sorption cycle is lost upon desorption in slightly amounts at the various RH intervals. The weight change value for the desorption cycle can be used along with the molecular weight of Compound I to calculate that no molecule of water is present in the crystal at 95% RH. This calculation assumes that no water is present in the sample at the 5% RH step at the end of the analysis. The post moisture sorption/desorption sample was identified as form A by XRPD. In separate experiments form A was stressed under various RH conditions at room temperature (Table 3A). After several weeks none of these samples had undergone a phase change. This is evident in the respective XRPD patterns for the samples, which all correspond to form A. The gradual mass increase/decrease observed throughout the range of RH levels examined in the moisture sorption/desorption profile coupled with the lack of a phase change for form A upon RH stress indicates that this solid phase may contain a variable amount of water that will be dependent on the RH of the environment. This type of hydrated phase is referred to as a variable or non-stoichiometric hydrate.

TABLE 2A

| Elapsed Time (min) | Weight (mg) | Weight chg (%) | Sample Temp (° C.) | Sample RH (%) |
|---|---|---|---|---|
| 0.1 | 12.164 | 0.000 | 25.20 | 9.14 |
| 14.1 | 12.164 | 0.002 | 25.20 | 5.18 |

TABLE 2A-continued

| Elapsed Time (min) | Weight (mg) | Weight chg (%) | Sample Temp (° C.) | Sample RH (%) |
|---|---|---|---|---|
| 21.1 | 12.164 | 0.001 | 25.22 | 14.96 |
| 28.2 | 12.164 | 0.001 | 25.20 | 24.97 |
| 35.2 | 12.164 | 0.002 | 25.20 | 35.05 |
| 42.2 | 12.164 | 0.004 | 25.20 | 44.89 |
| 51.2 | 12.168 | 0.035 | 25.19 | 54.85 |
| 60.2 | 12.168 | 0.039 | 25.21 | 64.93 |
| 69.2 | 12.169 | 0.041 | 25.20 | 74.86 |
| 78.2 | 12.169 | 0.045 | 25.21 | 84.87 |
| 87.2 | 12.170 | 0.049 | 25.21 | 94.56 |
| 97.0 | 12.166 | 0.019 | 25.21 | 85.20 |
| 105.7 | 12.166 | 0.017 | 25.21 | 75.06 |
| 114.7 | 12.165 | 0.016 | 25.21 | 65.04 |
| 123.7 | 12.165 | 0.014 | 25.21 | 55.13 |
| 131.7 | 12.165 | 0.012 | 25.22 | 45.01 |
| 139.7 | 12.165 | 0.008 | 25.21 | 34.97 |
| 146.7 | 12.168 | 0.035 | 25.22 | 24.96 |
| 153.7 | 12.167 | 0.032 | 25.21 | 14.97 |
| 163.7 | 12.163 | −0.004 | 25.20 | 4.82 |

TABLE 3A

Compound I Polymorph Screen - Solids-Based Experiments: Stress Studies using Glassy Materials

| Starting sample | Sample No. | Stress[a] | Duration | Habit[b] | XRPD File | Result |
|---|---|---|---|---|---|---|
| 1924-83-01[c] | 1924-83-04 | 81% RH | 9 days | colorless glass containing small, fine needles | — | — |
| 1924-83-02[c] | 1924-83-05 | 40° C. | 9 days | small blades | 100971 | form A |
| 1924-83-03[c] | 1924-83-06 | 79% RH/ 40° C. | 9 days | fine needles | 100972 | form A |
| 1966-09-01[c] | 1966-27-01 | 79% RH/ 60° C. | 1 hr | opaque irregularly shaped solids, unknown morphology | 109327 | form A |
| | 1966-27-02 | 79% RH/ 60° C. | 3 hrs | opaque irregularly shaped solids, unknown morphology | 109328[c] | form A |
| | 1966-27-03 | 79% RH/ 60° C. | 6.5 hrs | opaque irregularly shaped solids, unknown morphology | — | — |

[a]RH = relative humidity.
[b]Observations made visually or using polarized light microscopy.
[c]Samples considered non-GMP.

C. Method of Making Amorphous Form 1 of Compound I

Sample No. 1994-26-01: A slurry of Compound I was placed on a hot plate set at 80° C. The mixture was filtered through 0.2 μm nylon syringe filter into a warm vial. The vial was then placed on the hot plate, which was then set to 40° C. and the solution allowed to cool. Sufficient hexanes were added to cause a cloudy suspension to form. Fine solids were collected by filtration and allowed to air dry. The experiments yielded amorphous solids.

Sample No. 1994-07-01: Sufficient Compound I was added to methanol such that undissolved solids remained. The resulting slurry was filtered through 0.2 μm nylon syringe filter into a flask. The solution was evaporated to dryness using a rotary evaporator (Buchi, R-114) under reduced pressure. The amorphous solids were stored in desiccator.

Figure 5:
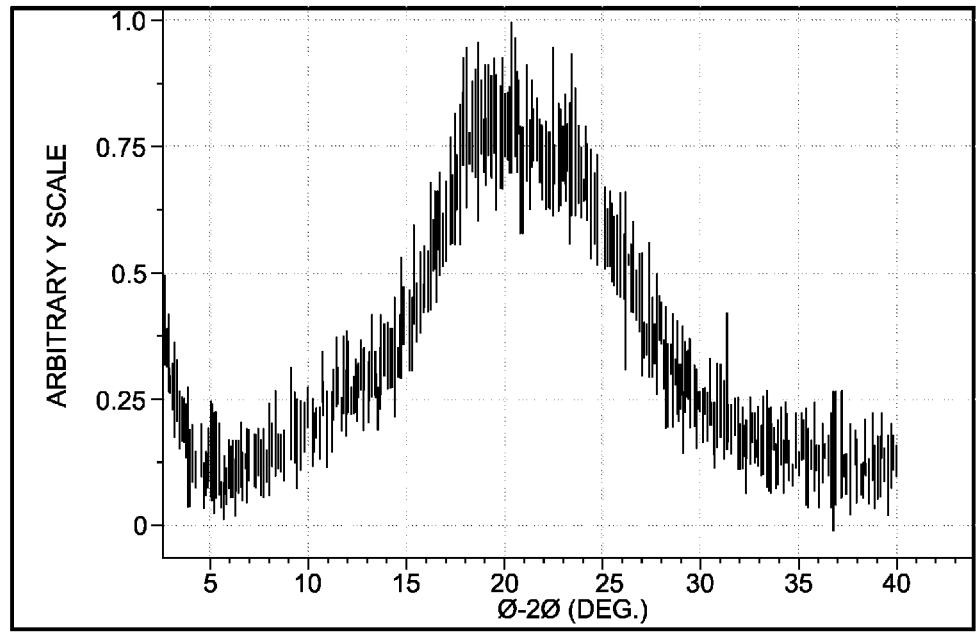
FIG. 5 illustrates the XRPD pattern of amorphous Form 1, wherein the "XRPD pattern" is a plot of the intensity of diffracted lines.

D. Characterization of Amorphous Form 1 of Compound I Polymorph Amorphous Form 1:

FIG. 5 illustrates the XRPD pattern of amorphous Form 1 (Sample No. 1994-12-01). The XRPD data show poor signal-to-noise ratio. The XRPD pattern tends to indicate that Form 1 is an amorphous form of Compound I.

Figure 6:
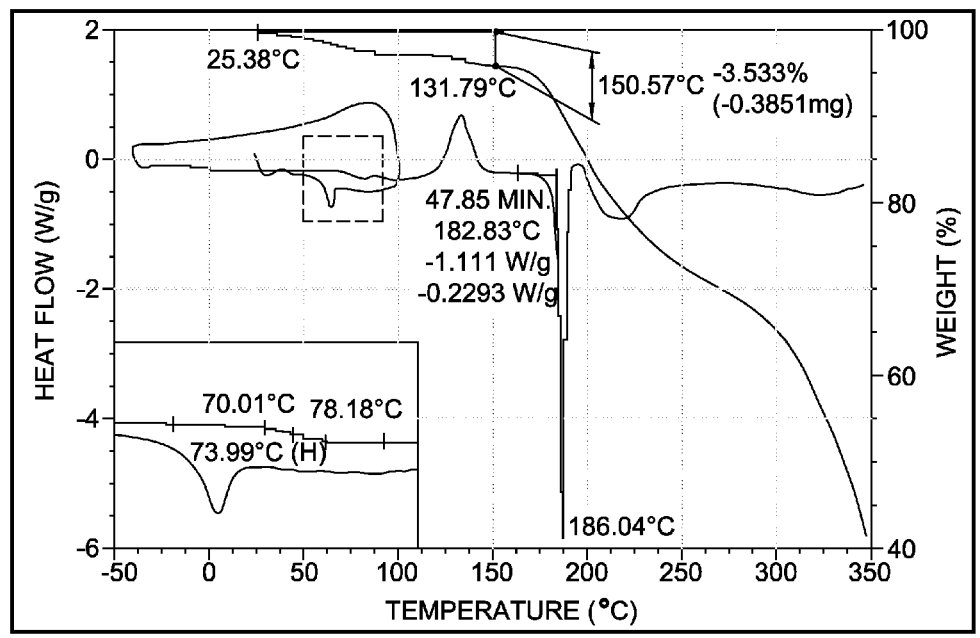
FIG. 6 is a plot of TGA data and the DSC data for amorphous Form 1.

Thermogravimetric and DSC data for amorphous Form 1 are summarized below in Table 1B and plotted in FIG. 6. Amorphous Form 1 was prepared by several methods as noted above. The material was very hygroscopic gaining 10% weight under 85% RH but lost weight above 85% RH, which is indicative of crystallization. The post moisture balance XRPD pattern matched form A. TGA weight loss was 4% between 25-168° C., probably due to adsorbed moisture. Therefore a cyclic DSC experiment was performed to dry the sample and then determine the glass transition temperature $T_g$, the onset of which was 70° C. An exothermic recrystallization event was recorded at 132° C., followed by a sharp endotherm at 183° C. (onset), which correlated with the onset of the melt (172° C.) determined by hot stage microscopy. This suggests that the amorphous solids crystallized to form A during heating.

TABLE 1B

Thermal Data for Amorphous Form 1

| Cyclic DSC Results | TGA Results |
|---|---|
| $T_g$ = 70° C. (onset)[1], Exotherm maxima at 132° C., Endotherm onset at 183° C. | 4% from 25-151° C. |

[1]$T_g$ = glass transition temperature

Figure 7:
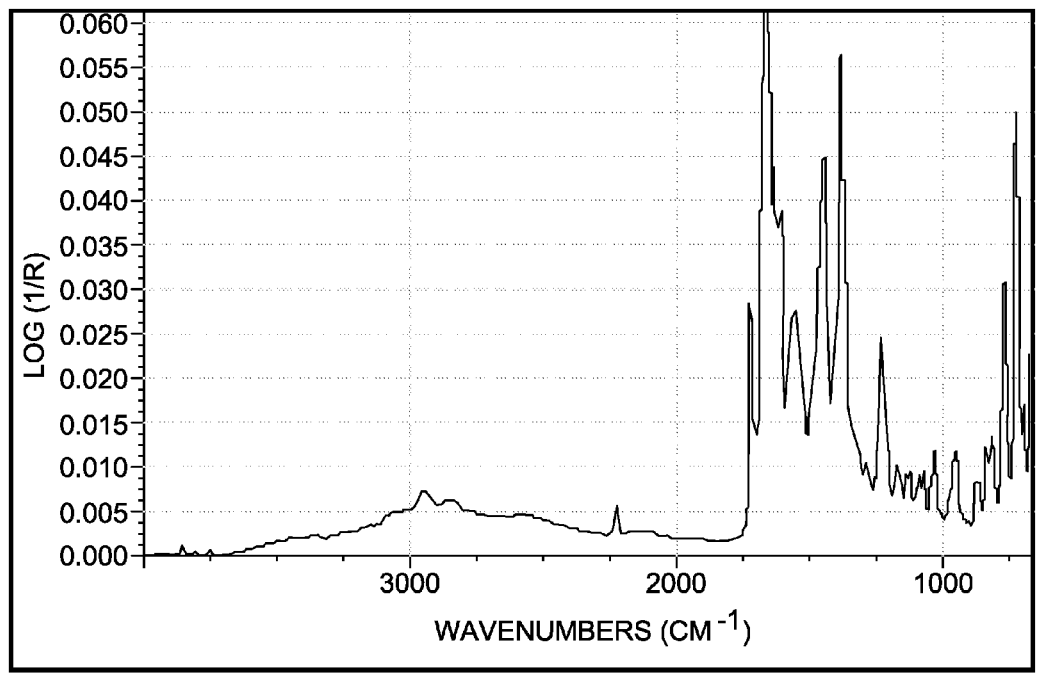
FIG. 7 is a plot of the IR absorption spectrum for amorphous Form 1.
Figure 8:
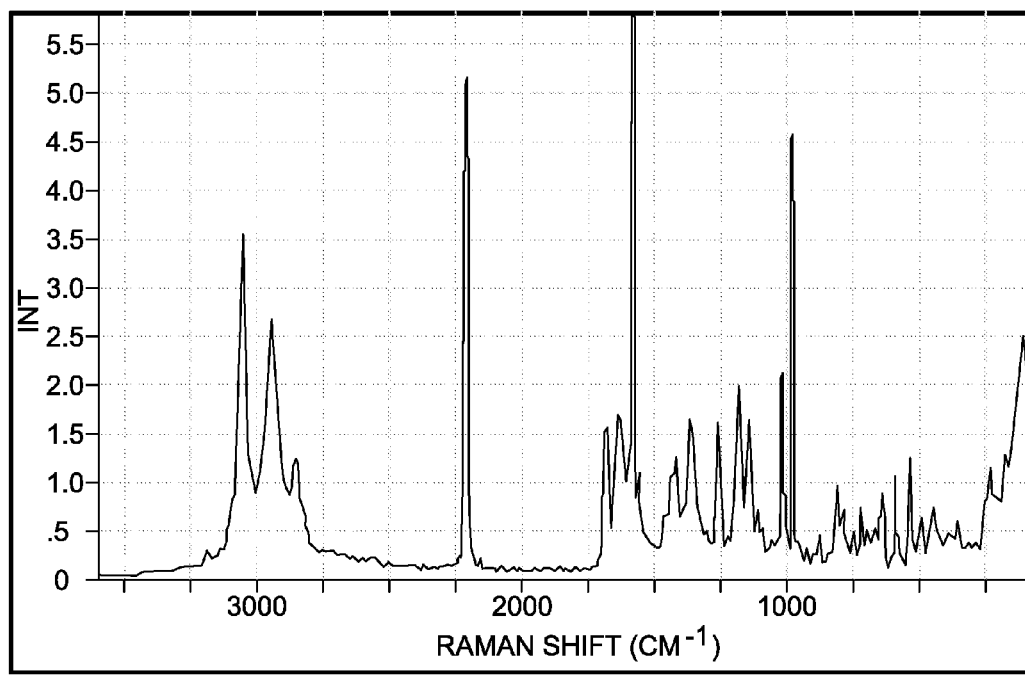
FIG. 8 is a plot of the FT-Raman absorption spectrum for amorphous Form 1.

The IR and FT-Raman spectra for amorphous Form 1 (sample no. 1994-07-01) are plotted in FIGS. 7 and 8, respectively.

Data regarding the moisture sorption/desorption properties of amorphous Form 1 are summarized in Table 2B below. The moisture sorption/desorption data show an initial weight loss of approximately 1% from ambient conditions to 5% RH and then a weight gain of about 6.5% between 5% and 95% RH. Between 85% and 95% RH the sample lost about 5% of weight, which is suggestive of a crystallization event. The sample recovered after the moisture sorption/desorption experiment was tentatively identified as containing form A.

TABLE 2B

| Elapsed Time (min) | Weight (mg) | Weight chg (%) | Sample Temp (° C.) | Sample RH (° C.) |
|---|---|---|---|---|
| 0.1 | 10.660 | 0.000 | 24.98 | 53.89 |
| 151.0 | 10.559 | −0.953 | 25.00 | 5.25 |
| 197.3 | 10.612 | −0.456 | 25.00 | 14.81 |
| 253.1 | 10.663 | 0.025 | 24.99 | 24.80 |
| 329.5 | 10.721 | 0.569 | 24.98 | 34.93 |
| 508.3 | 10.838 | 1.669 | 24.99 | 44.84 |
| 603.1 | 11.053 | 3.680 | 24.98 | 54.90 |
| 655.1 | 11.277 | 5.782 | 24.97 | 64.85 |
| 723.7 | 11.559 | 8.432 | 24.98 | 74.54 |
| 764.6 | 11.740 | 10.125 | 24.98 | 84.54 |
| 952.3 | 11.244 | 5.474 | 24.95 | 94.62 |
| 1139.9 | 11.017 | 3.348 | 24.98 | 85.49 |
| 1327.5 | 10.864 | 1.908 | 24.98 | 75.25 |
| 1517.0 | 10.730 | 0.655 | 24.98 | 65.12 |
| 1706.6 | 10.615 | −0.421 | 25.00 | 55.16 |
| 1894.1 | 10.532 | −1.208 | 25.01 | 45.08 |
| 2081.7 | 10.475 | −1.737 | 24.99 | 34.87 |
| 2199.9 | 10.453 | −1.946 | 24.99 | 24.87 |
| 2221.4 | 10.449 | −1.980 | 24.99 | 15.16 |
| 2238.3 | 10.446 | −2.007 | 24.99 | 5.06 |

4. Pharmaceutical Compositions Comprising Compound I Where at Least a Particular One of Form A or Amorphous Form 1 is Present The polymorphs of the present invention may be used in various pharmaceutical compositions. Such pharmaceutical compositions may comprise Compound I present in the composition in a range of between 0.005% and 100% (weight/weight), with the balance of the pharmaceutical composition comprising additional substances such as those described herein. In particular variations, the pharmaceutical composition comprises at least 0.25%, 0.5%, 1%, 5%, 10%, 25%, 50%, 75%, 80%, 85%, 90%, 95%, 97%, or 99% of Compound I. A given one of the polymorphic forms of Compound I may comprise at least 1%, 5%, 10%, 25%, 50%, 75%, 80%, 85%, 90%, 95%, 97%, or 99% of Compound I (weight/weight) in the pharmaceutical composition.

In general, the pharmaceutical compositions of the present invention may be prepared in a gaseous, liquid, semi-liquid, gel, or solid form, and formulated in a manner suitable for the route of administration to be used where at least a portion of Compound I is present in the composition in a particular polymorph form.

Pharmaceutical compositions according to the present invention may be adapted for administration by any of a variety of routes. For example, pharmaceutical compositions according to the present invention can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example, by catheter or stent), subcutaneously, intraadiposally, intraarticularly, or intrathecally, optionally in a slow release dosage form. In particular embodiments, the pharmaceutical compounds are administered orally, by inhalation or by injection subcutaneously, intramuscularly, intravenously or directly into the cerebrospinal fluid.

In addition to Compound I, the pharmaceutical composition may comprise one or more additional components that do not deleteriously affect the use of Compound I. For example, the pharmaceutical compositions may include, in addition to Compound I, conventional pharmaceutical excipients; diluents; lubricants; binders; wetting agents; disintegrating agents; glidants; sweetening agents; flavoring agents; emulsifying agents; solubilizing agents; pH buffering agents; perfuming agents; surface stabilizing agents; suspending agents; and other conventional, pharmaceutically inactive agents. In particular, the pharmaceutical compositions may comprise lactose, sucrose, dicalcium phosphate, carboxymethylcellulose, magnesium stearate, calcium stearate, talc, starch, natural gums (e.g., gum acaciagelatin, glucose, molasses, polyvinylpyrrolidine, celluloses and derivatives thereof), povidone, crospovidones acetate, sodium citrate, cyclodextrine derivatives, sorbitan monolaurate, triethanolamine sodium acetate, triethanolamine oleate, and other such agents. Methods of preparing such dosage forms are known in the art, and will be apparent to those skilled in this art; for example, see *Remington's Pharmaceutical Sciences,* 19th Ed. (Easton, Pa.: Mack Publishing Company, 1995). The pharmaceutical composition to be administered should, in any event, contain a sufficient quantity of Compound I to reduce dipeptidyl peptidases activity in vivo sufficiently to provide the desired therapeutic effect.

Compositions, according to the present invention, may be administered, or coadministered with other active agents. These additional active agents may include, for example, one or more other pharmaceutically active agents. Coadministration in the context of this invention is intended to mean the administration of more than one therapeutic agent, one of which includes Compound I. Such coadministration may also be coextensive, that is, occurring during overlapping periods of time or may be sequential, that is, occurring during non-overlapping periods of time.

The following are particular examples of oral, intravenous and tablet formulations that may optionally be used with Compound I. It is noted that these compositions may be varied depending on the indication for which the composition is to be used.

Exemplary capsule formulations are as follows:

| 12.5 mg of Compound I (weight of free base form) per tablet Core Tablet Formulation | |
|---|---|
| (1) 2-[[6-[(3R)-3-amino-1-piperidinyl]-3,4-dihydro-3-methyl-2,4-dioxo-1(2H)-pyrimidinyl]methyl]-benzonitrile (benzoate salt) | 17.0 mg |
| (2) Lactose Monohydrate, NF, Ph, Eur (FOREMOST 316 FAST FLO) | 224.6 mg |
| (3) Microcrystalline Cellulose, NF, Ph, Eur (AVICEL PH 102) | 120.1 mg |
| (4) Croscarmellose Sodium, NF, Ph, Eur (AC-DI-SOL) | 32.0 mg |
| (5) Colloidal Silicon Dioxide, NF, Ph, Eur (CAB-O-SIL M-5P) | 3.2 mg |
| (6) Magnesium Stearate, NF, Ph, Eur (MALLINCKRODT, Non-bovine Hyqual) | 3.2 mg |
| TOTAL (per tablet) | 400.0 mg |
| 25 mg of Compound I (weight of free base form) per tablet Core Tablet Formulation | |
| (1) 2-[[6-[(3R)-3-amino-1-piperidinyl]-3,4-dihydro-3-methyl-2,4-dioxo-1(2H)-pyrimidinyl]methyl]-benzonitrile (benzoate salt) | 34.0 mg |
| (2) Lactose Monohydrate, NF, Ph, Eur (FOREMOST 316 FAST FLO) | 207.6 mg |
| (3) Microcrystalline Cellulose, NF, Ph, Eur (AVICEL PH 102) | 120.1 mg |
| (4) Croscarmellose Sodium, NF, Ph, Eur (AC-DI-SOL) | 32.0 mg |
| (5) Colloidal Silicon Dioxide, NF, Ph, Eur (CAB-O-SIL M-5P) | 3.2 mg |

-continued

| | |
|---|---|
| (6) Magnesium Stearate, NF, Ph, Eur (MALLINCKRODT, Non-bovine Hyqual) | 3.2 mg |
| TOTAL (per tablet) | 400.0 mg |

50 mg of Compound I (weight of free base form) per tablet
Core Tablet Formulation

| | |
|---|---|
| (1) 2-[[6-[(3R)-3-amino-1-piperidinyl]-3,4-dihydro-3-methyl-2,4-dioxo-1(2H)-pyrimidinyl]methyl]-benzonitrile (benzoate salt) | 68.0 mg |
| (2) Lactose Monohydrate, NF, Ph, Eur (FOREMOST 316 FAST FLO) | 173.6 mg |
| (3) Microcrystalline Cellulose, NF, Ph, Eur (AVICEL PH 102) | 120.1 mg |
| (4) Croscarmellose Sodium, NF, Ph, Eur (AC-DI-SOL) | 32.0 mg |
| (5) Colloidal Silicon Dioxide, NF, Ph, Eur (CAB-O-SIL M-5P) | 3.2 mg |
| (6) Magnesium Stearate, NF, Ph, Eur (MALLINCKRODT, Non-bovine Hyqual) | 3.2 mg |
| TOTAL (per tablet) | 400.0 mg |

Film Coat (12.0 mg in total)
(1) Opadry II 85F18422, White - Portion 1 (COLORCON)
(2) Opadry II 85F18422, White - Portion 2 (COLORCON)
(3) Opadry II 85F18422, White - Portion 3 (COLORCON)

Exemplary intravenous and tablet formulations are as follows:

| INTRAVENOUS FORMULATION | |
|---|---|
| Compound of the Present Invention | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

| TABLET FORMULATION | |
|---|---|
| Compound of the Present Invention | 1% |
| Microcrystalline Cellulose | 73% |
| Stearic Acid | 25% |
| Colloidal Silica | 1% |

Provided in the examples are, by way of illustration but not limitation, more particular examples of formulations incorporating one or more of Form A or amorphous Form 1.

5. Indications for Use of Compound I

In one embodiment, Compound I and compositions, kits and articles of manufacture comprising Compound I are used to inhibit DPP-IV. Compound I and compositions, kits and articles of manufacture comprising Compound I are also used to treat a disease state for which DPP-IV possesses activity that contributes to the pathology and/or symptomology of the disease state.

Compound I may be administered to a subject wherein DPP-IV activity within the subject is altered, preferably reduced.

In another embodiment, a therapeutic method is provided that comprises administering Compound I. In another embodiment, a method of inhibiting cell proliferation is provided that comprises contacting a cell with an effective amount of Compound I. In another embodiment, a method of inhibiting cell proliferation in a patient is provided that comprises administering to the patient a therapeutically effective amount of Compound I.

In another embodiment, a method of treating a condition in a patient which is known to be mediated by DPP-IV, or which is known to be treated by DPP-IV inhibitors, comprising administering to the patient a therapeutically effective amount of Compound I. In another embodiment, a method is provided for using Compound I in order to manufacture a medicament for use in the treatment of disease state which is known to be mediated by DPP-IV, or which is known to be treated by DPP-IV inhibitors.

In another embodiment, a method is provided for treating a disease state for which DPP-IV possesses activity that contributes to the pathology and/or symptomology of the disease state, the method comprising: administering Compound I to a subject such that the free base form of Compound I is present in the subject in a therapeutically effective amount for the disease state.

In another embodiment, a method is provided for treating a cell proliferative disease state comprising administering Compound I so that cells are treated with the free base form of Compound I in combination with an anti-proliferative agent, wherein the cells are treated with the free base form of Compound I, at the same time, and/or after the cells are treated with the anti-proliferative agent, referred to herein as combination therapy. It is noted that treatment of one agent before another is referred to herein as sequential therapy, even if the agents are also administered together. It is noted that combination therapy is intended to cover when agents are administered before or after each other (sequential therapy) as well as when the agents are administered at the same time.

Examples of diseases that may be treated by administration of Compound I and compositions according to the present invention include, but are not limited to conditions mediated by DPP-IV, in particular diabetes, more particular type 2 diabetes mellitus, diabetic dislipidemia, conditions of impaired glucose tolerance (IGT), conditions of impaired fasting plasma glucose (IFG), metabolic acidosis, ketosis, appetite regulation, obesity, immunosuppressants or cytokine release regulation, autoimmune diseases such as inflammatory bowel disease, multiple sclerosis and rheumatoid arthritis, AIDS, cancers (prevention of metastases, for example, breast and prostrate tumors to the lungs), dermatological diseases such as psoriasis and lichen planus, treatment of female infertility, osteoporosis, male contraception and neurological disorders.

6. Kits and Articles of Manufacture Comprising Compound I Polymorphs

The present invention is also directed to kits and other articles of manufacture for treating diseases associated with dipeptidyl peptidases. It is noted that diseases are intended to cover all conditions for which the dipeptidyl peptidases possesses activity that contributes to the pathology and/or symptomology of the condition.

In one embodiment, a kit is provided that comprises a pharmaceutical composition comprising Compound I where greater than 1%, 5%, 10%, 25%, 50%, 75%, 80%, 85%, 90%, 95%, 97% or 99% of Compound I (by weight) is present in the composition as a particular one of Form A or amorphous Form 1; and instructions for use of the kit. Optionally, the composition comprises at least 0.25%, 0.5%, 1%, 5%, 10%, 25%, 50%, 75%, 80%, 85%, 90%, 95%, 97%, or 99% of Compound I. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a pharmaceutical composition comprising Compound I where greater than 1%, 5%, 10%, 25%, 50%, 75%, 80%, 85%, 90%, 95%, 97% or 99% of Compound I (by weight) is present in the composition as a particular one of Form A or amorphous Form 1; and packaging materials. Optionally, the composition comprises at least 0.25%, 0.5%, 1%, 5%, 10%, 25%, 50%, 75%, 80%, 85%, 90%, 95%, 97%, or 99% of Compound I. The packaging material may comprise a container for housing the composition. The container may optionally comprise a label indicating the disease state for which the composition is to be administered, storage information, dosing information and/or instructions regarding how to administer the composition. The article of manufacture may also optionally comprise additional components, such as syringes for administration of the composition. The article of manufacture may comprise the composition in single or multiple dose forms.

It is noted that the packaging material used in kits and articles of manufacture according to the present invention may form a plurality of divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container that is employed will depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box. Typically the kit includes directions for the administration of the separate components. The kit form is particularly advantageous when the separate components are preferably administered in different dosage forms (e.g., oral, topical, transdermal and parenteral), are administered at different dosage intervals, or when titration of the individual components of the combination is desired by the prescribing physician.

One particular example of a kit according to the present invention is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter that indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

7. Dosage Forms

Compositions according to the present invention are optionally provided for administration to humans and animals in unit dosage forms or multiple dosage forms, such as tablets, capsules, pills, powders, dry powders for inhalers, granules, sterile parenteral solutions or suspensions, oral solutions or suspensions, and oil-water emulsions containing suitable quantities Compound I. Unit-dose forms, as used herein, refers to physically discrete units suitable for human and animal subjects and packaged individually as is known in the art. Each unit-dose contains a predetermined quantity of Compound I sufficient to produce the desired therapeutic effect, in association with a pharmaceutical carrier, vehicle or diluent. Examples of unit-dose forms include ampoules and syringes, and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules, or bottles of pints or gallons. Hence, multiple dose form may be viewed as a multiple of unit-doses that are not segregated in packaging.

In general, the total amount of Compound I in a pharmaceutical composition according to the present invention should be sufficient to a desired therapeutic effect. This amount may be delivered as a single per day dosage, multiple dosages per day to be administered at intervals of time, or as a continuous release dosage form. Dosage forms or compositions may optionally comprise Compound I in the range of 0.005% to 100% (weight/weight) with the balance comprising additional substances such as those described herein. For oral administration, a pharmaceutically acceptable composition may optionally comprise any one or more commonly employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum. Such compositions include solutions, suspensions, tablets, capsules, powders, dry powders for inhalers and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparing these formulations are known to those skilled in the art. The compositions may optionally contain 0.01%-100% (weight/weight) of Compound I, optionally 0.1-95%, and optionally 1-95%. Compositions according to the present invention are optionally provided for administration to humans and animals in unit dosage forms, such as tablets, capsules, pills, powders, dry powders for inhalers, granules, sterile parenteral solutions or suspensions, and oral solutions or suspensions, and oil-water emulsions containing suitable quantities of the compounds, particularly the pharmaceutically acceptable salts, preferably the sodium salts, thereof. The pharmaceutically therapeutically active compounds and derivatives thereof are typically formulated and administered in unit-dosage forms or multiple-dosage forms. Unit-dose forms, as used herein, refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes individually packaged tablet or capsule. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pint or gallons. Hence, multiple dose form is a multiple of unit-doses that are not segregated in packaging. Dosage forms or compositions may optionally comprise Compound I in the range of 0.005% to 100% (weight/weight) with the balance comprising additional substances such as those described herein. For oral administration, a pharmaceutically acceptable composition may optionally comprise any one or more commonly employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum. Such compositions include solutions, suspensions, tablets, capsules, powders, dry powders for inhalers and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparing these formulations are known to those skilled in the art. The compositions may optionally contain 0.01%-100% (weight/weight) of Compound I, optionally 0.1-95%, and optionally 1-95%.

In one embodiment, the pharmaceutical composition is a pill or capsule adapted for oral administration. In another embodiment, the pharmaceutical composition is in an oral dosage form selected from the group consisting of pills, tablets, capsules, emulsions, suspensions, microsuspensions, wafers, sprinkles, chewing gum, powders, lyophilized powders, granules, and troches. In still another embodiment, the pharmaceutical composition is in a parenteral dosage form selected from the group consisting of suspensions, microsuspensions, emulsions, solid forms suitable for suspension or emulsification prior to injection, and implantable devices. In yet another embodiment, the pharmaceutical composition is adapted for topical or transdermal administration. In a further embodiment, the pharmaceutical composition is in a topical or transdermal dosage form selected from the group consisting of suspensions, microsuspensions, emulsions, creams, gels, ointments, lotions, tinctures, pastes, powders, foams, aerosols, irrigations, sprays, suppositories, bandages, and dermal patches. In still a further embodiment, the pharmaceutical composition is in a pulmonary dosage form selected from the group consisting of powders, aerosols, suspensions, microsuspensions, and emulsions.

A. Formulations for Oral Administration

Oral pharmaceutical dosage forms may be as a solid, gel or liquid where Compound I is retained in one of the polymorphic forms. Examples of solid dosage forms include, but are not limited to tablets, capsules, granules, and bulk powders. More specific examples of oral tablets include compressed, chewable lozenges and tablets that may be enteric-coated, sugar-coated or film-coated. Examples of capsules include hard or soft gelatin capsules. Granules and powders may be provided in non-effervescent or effervescent forms. Each may be combined with other ingredients known to those skilled in the art.

In certain embodiments, Compound I is provided as solid dosage forms, preferably capsules or tablets. The tablets, pills, capsules, troches and the like may optionally contain one or more of the following ingredients, or compounds of a similar nature: a binder; a diluent; a disintegrating agent; a lubricant; a glidant; a sweetening agent; and a flavoring agent.

Examples of binders that may be used include, but are not limited to, microcrystalline cellulose, gum tragacanth, glucose solution, acacia mucilage, gelatin solution, sucrose and starch paste.

Examples of lubricants that may be used include, but are not limited to, talc, starch, magnesium or calcium stearate, lycopodium and stearic acid.

Examples of diluents that may be used include, but are not limited to, lactose, sucrose, starch, kaolin, salt, mannitol and dicalcium phosphate.

Examples of glidants that may be used include, but are not limited to, colloidal silicon dioxide.

Examples of disintegrating agents that may be used include, but are not limited to, crosscarmellose sodium, sodium starch glycolate, alginic acid, corn starch, potato starch, bentonite, methylcellulose, agar and carboxymethylcellulose.

Examples of coloring agents that may be used include, but are not limited to, any of the approved certified water soluble FD and C dyes, mixtures thereof; and water insoluble FD and C dyes suspended on alumina hydrate.

Examples of sweetening agents that may be used include, but are not limited to, sucrose, lactose, mannitol and artificial sweetening agents such as sodium cyclamate and saccharin, and any number of spray-dried flavors.

Examples of flavoring agents that may be used include, but are not limited to, natural flavors extracted from plants such as fruits and synthetic blends of compounds that produce a pleasant sensation, such as, but not limited to peppermint and methyl salicylate.

Examples of wetting agents that may be used include, but are not limited to, propylene glycol monostearate, sorbitan monooleate, diethylene glycol monolaurate and polyoxyethylene lauryl ether.

Examples of anti-emetic coatings that may be used include, but are not limited to, fatty acids, fats, waxes, shellac, ammoniated shellac and cellulose acetate phthalates.

Examples of film coatings that may be used include, but are not limited to, hydroxyethylcellulose, sodium carboxymethylcellulose, polyethylene glycol 4000 and cellulose acetate phthalate.

If oral administration is desired, Compound I may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it may optionally additionally comprise a liquid carrier such as a fatty oil. In addition, dosage unit forms may optionally additionally comprise various other materials that modify the physical form of the dosage unit, for example, coatings of sugar and other enteric agents.

Compound I may also be administered as a component of an elixir, suspension, syrup, wafer, sprinkle, chewing gum or the like. A syrup may optionally comprise, in addition to the active compounds, sucrose as a sweetening agent and certain preservatives, dyes and colorings and flavors.

It is understood that the precise dosage and duration of treatment will be a function of the location of where the composition is parenterally administered, the carrier and other variables that may be determined empirically using known testing protocols or by extrapolation from in vivo or in vitro test data. It is to be noted that concentrations and dosage values may also ultimately depend on, among other criteria known to those of skill in the art, the age, weight and condition of the patient or animal, as is known in the art. It is to be further understood that for any particular subject, specific dosage regimens may need to be adjusted over time according to the individual need and the professional judgment of the person administering or supervising the administration of the formulations. Hence, the concentration ranges set forth herein are intended to be exemplary and are not intended to limit the scope or practice of the claimed formulations.

Examples

Example 1

Preparation of Compound I

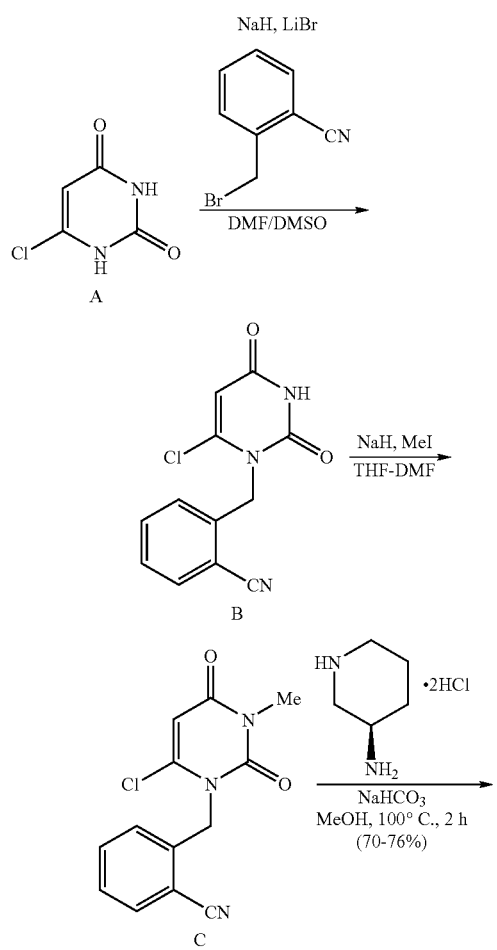

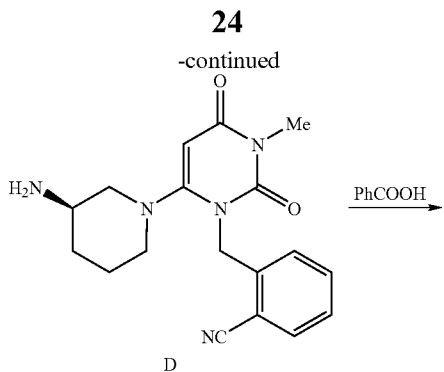

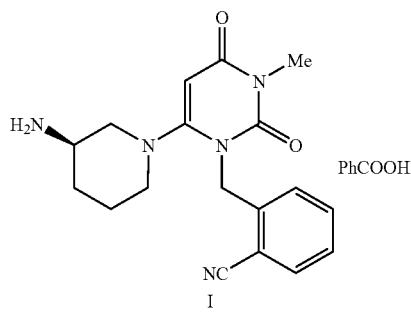

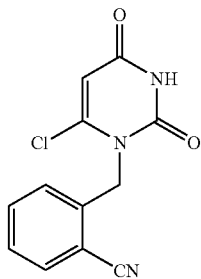

2-(6-Chloro-2,4-dioxo-3,4-dihydro-2H-pyrimidin-1-ylmethyl)-benzonitrile (B)

To a solution of 6-chlorouracil (20 g, 122 mmol) in a mixture of DMF-DMSO (6:1, 600 mL) under nitrogen at 0° C., was added sodium hydride (60%, 5.5 g, 137 mmol) in portions. After 0.5h, lithium bromide (8 g, 96 mmol) was added into the mixture and stirred for 15 min at 0° C. A solution of α-Bromo-o-tolunitrile (25.1 g, 128 mmol) in DMF (30 mL) was added dropwise, and stirred at this temperature for 1 h, and then RT overnight. The mixture was evaporated and co-evaporated with water in vacuo to remove most of DMF, and then poured into ice water (1L). The precipitate was collected by filtration. The crude product was suspended in hot AcOEt-CHCl$_3$ and sonicated for 5 min, allowed to stand at 0° C. for 1 h, and then filtered to give a white solid of the title compound (19 g) in 54% yield. $^1$H-NMR(400 MHz, DMSO): δ 11.82 (s, 1H), 7.87 (d, 1H, J=7.6 Hz), 7.71 (t, 1H, J=7.6 Hz), 7.51 (t, 1H, J=7.6 Hz), 7.37 (d, 1H, J=8 Hz), 6.06 (s, 1H), 5.31 (s, 2H). MS (ES) [m+H] calc'd for $C_{12}H_9ClN_3O_2$, 262.0.

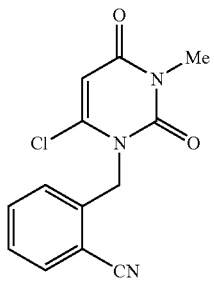

2-(6-Chloro-3-methyl-2,4-dioxo-3,4-dihydro-2H-pyrimidin-1-ylmethyl)-benzonitrile (C)

To a cold (0° C.) solution of benzylated 6-chlorouracil 2 (10 g, 38 mmol) in DMF-THF (1:1, 300 mL) under nitrogen, was added NaH (60%, 1.6 g, 39.9 mmol) in portions, followed by adding LiBr (2 g). The mixture was stirred at r.t for 20 min. After adding iodomethane (5.4 mL, 76 mmol), the flask was sealed and stirred at this temperature for 10 min, rt for 2 h, and 35° C. overnight, and then concentrated in vacuo. The residue was dissolved in $CHCl_3$ and washed with water and brine, dried ($Na_2SO_4$), and filtered then concentrated in vacuo. The crude product was crystallized from THF-Hexanes to give 7.6 g (72%) of the title compound 3. $^1H$ NMR (400 MHz, DMSO): δ 7.87 (d, 1H, J=7.6 Hz), 7.70 (t, 1H, J=7.6 Hz), 7.51 (t, 1H, J=7.6 Hz), 7.40 (d, 1H, J=8 Hz), 6.21 (s, 1H), 5.38 (s, 2H), 3.28 (s, 3H). MS (ES) [m+H] calc'd for $C_{13}H_{11}ClN_3O_2$, 276.1; found 276.1.

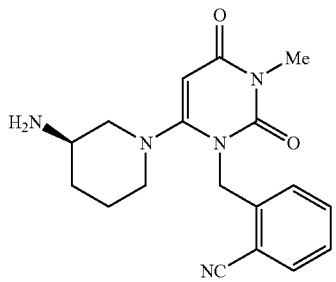

2-{6-[3(R)-Amino-piperidin-1-yl]-3-methyl-2,4-dioxo-3,4-dihydro-2H-pyrimidin-1-ylmethyl}-benzonitrile (D). 2-(6-Chloro-3-methyl-2,4-dioxo-3,4-dihydro-2-H-pyrimidin-1-ylmethyl)-benzonitrile (330 mg, 1.08 mmol), (R)-3-amino-piperidine dihydrochloride (246 mg, 1.4 mmol) and sodium bicarbonate (500 mg, 5.4 mmol) were stirred with 200 mg activated molecular sieves (4A) in dry MeOH (5 mL) at 100° C. for 2 h. The reaction was filtered through Celite, concentrated in vacuo, and then diluted with $CHCl_3$, and washed with water. The water phase was extracted with $CHCl_3$ and the combined organic phases were washed with water, dried ($Na_2SO_4$), and filtered. TFA (1 mL) was added into the solution which was then concentrated in vacuo. The residue was dissolved in a small amount of MeOH, and $Et_2O$ was added to force precipitation. The mixture was allowed to stand at RT overnight. Solvents were decanted, and the solid was washed with $Et_2O$ two times to give 270 mg product as off-white powder. $^1H$-NMR (400 MHz, $CDCl_3$-$CD_3OD$ 10:1): δ 7.82 (d, 1H, J=7.6 Hz), 7.65 (t, 1H, J=7.6 Hz), 7.46 (t, 1H, J=7.6 Hz), 7.23 (d, 1H, J=8.0 Hz), 5.42 (s, 1H), 5.50-5.00 (ABq, 2H, J=41.6, 15.2 Hz), 3.30 (m, 2H), 3.16 (s, 3H), 2.91 (m, 1H), 2.76 (m, 2H), 1.93 (m, 1H), 1.79 (m, 1H), 1.51 (m, 2H). MS (ES) [m+H] calc'd for $C_{18}H_{22}N_5O_2$, 340.2; found, 340.2.

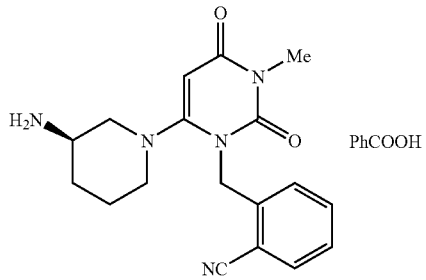

The benzoic acid salt was formed by treating the benzonitrile product (D) with benzoic acid to form 2-[6-(3-amino-piperidin-1-yl)-3-methyl-2,4-dioxo-3,4-dihydro-2H-pyrimidin-1-ylmethyl]-benzonitrile benzoate. Preparation and isolation of the benzoate salt was performed by conventional methods for the formation of acid addition salts. $^1H$-NMR (400 MHz, $CDCl_3$-$CD_3OD$ 10:1): δ 7.82 (d, 1H, J=7.6 Hz), 7.65 (t, 1H, J=7.6 Hz), 7.46 (t, 1H, J=7.6 Hz), 7.23 (d, 1H, J=8.0 Hz), 5.42 (s, 1H), 5.50-5.00 (ABq, 2H, J=41.6, 15.2 Hz), 3.30 (m, 2H), 3.16 (s, 3H), 2.91 (m, 1H), 2.76 (m, 2H), 1.93 (m, 1H), 1.79 (m, 1H), 1.51 (m, 2H). MS (ES) [m+H] calc'd for $C_{18}H_{22}N_5O_2$, 340.2; found, 340.2.

Example 2

Characterization of Solubility of Compound I in Different Solvents

The following experiments were performed in order to determine the solubility of Compound I in different solvents and solvent systems. This information was later used to identify potential crystallization conditions for Compound I.

Materials and Reagents

Unless otherwise stated Compound I Form A and amorphous material prepared from this sample were used as the starting materials for all crystallization experiments. Solvents and other reagents were of ACS or HPLC grade and were used as received.

Solubility Estimates

A weighed sample of Compound I was treated with aliquots of the test solvent at room temperature. The mixture was sonicated between aliquot additions to facilitate dissolution. Complete dissolution of the test material was determined by visual inspection. Solubilities were estimated from these experiments based on the total solvent used to provide complete dissolution. The actual solubility may be greater than those calculated because of the use of solvent aliquots that were too large or due to a slow rate of dissolution. The solubility is expressed as "less than" if dissolution did not occur during the experiment. If complete dissolution was achieved as a result of only one aliquot addition, the solubility is expressed as "greater than."

TABLE 4

Solubility Estimates for Compound I Form A

| Solvent | Sample No. | Solubility (mg/mL)[a] |
|---|---|---|
| acetone | 1924-78-02 | <3 |
| CAN | 1924-78-05 | <1 |
| $CH_2Cl_2$ | 1924-78-03 | <3 |
| DMF | 1924-77-07 | 6 |
| dioxane | 1924-78-06 | <1 |
| EtOH | 1924-77-02 | <3 |
| EtOAc | 1924-78-01 | <3 |
| IPA | 1924-77-03 | <1 |
| MeOH | 1924-77-01 | 13 |
| MEK | 1924-77-05 | 3 |
| MIBK | 1924-77-06 | <3 |
| THF | 1924-78-04 | <1 |
| water | 1924-77-04 | 8 |

[a]Approximate solubilities rounded to nearest whole number.

Form A polymorph was found to be soluble in water (8 mg/mL), methanol (13 mg/mL), dimethylformide (6 mg/mL), methyl ethyl ketone (3 mg/mL) and acetone, dichloromethane, ethanol, ethyl acetate and methyl isobutyl ketone, all at <3 mg/mL). Thermal analysis indicates that this solid phase is thermally stable above 172° C. DSC analysis and melting point determinations determined that Form A melts at around 172° C. Moisture sorption/desorption analysis of form A demonstrates that this polymorph is a variable hydrate.

TABLE 5

Compound I Polymorph Screen - Solution-Based Experiments

| Solvent | Conditions[a] | Sample No. | Result |
|---|---|---|---|
| — | milled form A for 15 min/30 Hz at RT | 1966-04-01 | disordered form A |
| — | milled form A 30 min/30 Hz at RT | 1966-04-02 | disordered form A |
| | | | disordered form A[c] |
| water | wet milled form A at 30 Hz for 20 mins | 2012-22-01 | form A |
| | | | form A |
| | wet milled amorphous at 30 Hz for 5 mins | 1994-89-02 | form A |
| — | freeze mill 3 × 2 min@10 Hz | 1966-35-01 | disordered form A |
| acetone | FE | 1924-73-02 | form A |
| | SE | 1924-73-07 | disordered from A |
| | SC (45° C.) | 1924-69-06[d] | — |
| | | 1924-94-02[d] | — |
| | SE of 1924-94-02 | 1966-16-04[d] | — |
| | RE (40° C.) | 1924-83-02 | — |
| | RT slurry | 1924-97-05 | form A |
| ACN | FE | 1924-71-09 | — |
| | SE | 1966-14-03 | — |
| ACN | SC (60° C.) | 1924-67-05 | form A |
| | RT slurry | 1924-97-09 | form A |
| | 60° C. slurry | 1924-98-03 | form A |
| butanol | FE | 1924-71-01 | — |
| | SE | 1924-74-03 | form A |
| | SC (60° C.) | 1924-66-02 | — |
| | | 1924-93-03 | — |
| | | 1966-16-02 | — |
| | RT slurry | 1924-97-07 | form A |
| | 60° C. slurry | 1924-98-02 | form A |
| $CH_2Cl_2$ | FE | 1924-73-01 | — |
| | SE | 1924-73-06 | — |
| | | 1966-24-01 | — |
| | SC (45° C.) | 1924-69-05[c] | — |
| | | 1924-94-01[c] | — |
| | RE (40° C.) | 1924-83-03 | — |
| | RT slurry | 1924-97-04 | — |
| DMF | FE | 1924-73-05 | — |
| | 1924-73-05 in 40° C. oven | 1966-18-01 | — |
| | CE | 1966-29-01 | — |
| | | 1966-29-02 | — |
| | | 1966-29-03 | — |
| | SC (60° C.) | 1924-69-01[c] | — |
| | | 1924-93-04[c] | — |
| | | 1966-16-03[c] | — |
| DMSO | FE | 1966-72-04 | form A |
| dioxane | FE | 1924-71-08 | — |
| | SE | 1966-31-01 | — |
| | CE | 1966-29-04 | — |
| | | 1966-29-05 | — |
| | SC (60° C.) | 1924-67-03 | form A |
| | RT slurry | 1924-97-03 | form A |
| EtOH | FE | 1924-73-04 | form A |
| | SE | 1924-73-09 | form A |
| | | 1966-15-01[c] | — |
| | CE | 1966-30-01 | — |
| | | 1966-30-02 | — |
| | | 1966-30-03 | — |
| | SC (60° C.) | 1924-69-03[c] | — |
| | | 1924-93-05[c] | form A |
| | RT slurry | 1924-97-08 | form A |
| EtOH-IPA | RE, evaporation | 1966-71-02 | form A |
| EtOH-water | SC (60° C.) | 1966-93-01 | — |
| | SC (80° C.) | 1966-61-01 | — |
| | | 1966-75-02 | — |
| | | 1994-25-01 | form A |
| EtOAc | FE | 1924-71-04 | form A |
| | SE | 1924-74-05 | disordered form A |
| | | 1966-14-04 | — |
| EtOAc | SC (60° C.) | 1924-67-06 | — |
| | RT slurry | 1924-97-11 | form A |
| | 60° C. slurry | 1924-98-04 | form A |
| | VS | 1966-79-02 | — |
| heptane | FE | 1924-71-07 | — |
| | FE, 60° C. (1924-93-02) | 1966-16-01 | — |
| | SC (60° C.) | 1924-66-01 | — |
| | | 1924-93-02 | — |
| | RT slurry | 1924-97-06 | form A |
| IPA | FE | 1924-71-11 | — |
| | | 1924-92-02[c] | — |
| | SE | 1924-74-04 | form A |
| | SC (60° C.) | 1924-69-02[c] | form A |
| | RT slurry | 1924-97-02 | form A |
| | 60° C. slurry | 1924-98-01 | form A |
| | VS | 1966-79-01 | — |
| IPOAc | FE | 1966-50-01 | — |
| IPOAc | SC (60° C.) | 1966-50-02 | — |
| | SC (80° C.) | 1994-26-02 | form A |
| MeOH | FE | 1924-73-03 | — |
| | | 1924-93-01[c] | — |
| | | 1994-10-01 | — |
| | | 1994-10-02 | — |
| | | 1994-10-03 | — |
| | | 1994-10-04 | — |
| | SE | 1924-73-08 | form A |
| | CE | 1966-29-06 | — |
| | | 1966-29-07 | — |
| | SC (60° C.) | 1924-69-04[c] | form A |
| | 60° C. slurry | 1924-98-05 | form A |
| | RE | 1924-83-01 | — |
| | | 1966-09-01 | form A endotherms: 187, 211° C. |
| | | 1966-73-01 | — |
| | | 1966-73-02 | — |
| | | 1966-73-03 | — |
| | | 1994-07-01 | amorphous |

TABLE 5-continued

Compound I Polymorph Screen - Solution-Based Experiments

| Solvent | Conditions[a] | Sample No. | Result |
|---|---|---|---|
| | RE, vac. | 1966-76-01 | form A + amorphous |
| | RE at RT | 1994-89-01 | amorphous |
| MEK | FE | 1924-71-10 | — |
| | | 1924-92-01 | — |
| | SE | 1924-74-01 | — |
| | SC (60° C.) | 1924-67-07 | form A |
| MIBK | FE | 1924-71-05 | form A |
| | SE | 1966-14-02 | — |
| | CE | 1966-29-08 | — |
| | | 1966-29-09 | — |
| | | 1966-29-10 | — |
| | SC (60° C.) | 1924-67-02 | — |
| NO$_2$Me | FE | 1966-72-03 | — |
| TFE | VS | 1966-79-03 | — |
| | FE | 1966-72-01 | — |
| | SE | 1966-72-02 | — |
| | | 1994-31-01 | — |
| | RE, 40° C. oven | 1994-02-01 | form A |
| THF | FE | 1924-71-02 | — |
| | SE | 1924-73-10 | — |
| | SC (60° C.) | 1924-67-04 | form A |
| | RT slurry | 1924-97-01 | form A |
| toluene | FE | 1924-71-03 | — |
| | SE | 1966-14-01 | — |
| | SC (60° C.) | 1924-66-03 | — |
| | RT slurry | 1924-97-10 | form A |
| water | FE | 1924-71-06 | amorphous |
| | SE | 1924-74-02 | form A |
| | SC (60° C.) | 1924-67-01 | — |
| | SC (80° C.) | 1966-64-01 | — |
| water | RE | 1966-75-01 | form A |
| | RE | 1966-44-01 | form A |
| | lyophilization | 1994-12-01 | amorphous |
| | | 2035-15-01 | amorphous |

[a]FE = fast evaporation, SE = slow evaporation, SC = slow cool, RT = room temperature, VS = vapor stress, RE = rotary evaporator.
b. B = birefringence, E = extinction. Observations made visually or using polarized light microscopy.
[c]Samples considered non-GMP.
§ = non-GMP observations.

Sample Preparation

General Methods

Slow Evaporation (SE): Form A was added to solvents of interest. Sonication was used to aid in dissolution. Once the mixture dissolved, as judged by visual inspection, the solution was passed through 0.2-μm nylon filter into a clean vial, covered with aluminum foil and perforated. The solution was allowed to evaporate under ambient conditions.

Fast Evaporation (FE): Samples were prepared according to the method for slow evaporation, except that solutions were left uncovered to evaporate.

Slow Cool (SC): Concentrated solutions of Form A were prepared in various solvents at ambient or at elevated temperature. The concentrated solutions were filtered through 0.2-μm nylon filters into clean vials. The solutions were allowed to slowly cool to room temperature. Further cooling to sub-ambient temperatures was achieved by placing samples in a refrigerator or freezer.

Fast Cool (FC): Concentrated solutions of Form A were prepared in various solvents at elevated temperatures. The concentrated solutions were filtered through 0.2-μm nylon filters into clean vials. The solutions were removed from the heat source and placed at room temperature. Further cooling to sub-ambient temperatures was achieved by placing samples in a refrigerator or freezer.

Rotary Evaporation (RE): Concentrated solutions of Form A were prepared in various test solvents. Solutions were passed through 0.2-μm nylon filters into clean containers, and samples were stripped to dryness using a Büchi R-114 rotavapor. Samples were immersed and rotated in a water bath at 30 or 40° C. set point during evaporation.

Crash Precipitation (CP): A concentrated solution of Form A was prepared in different solvents at elevated temperature. Solutions were passed through 0.2-μm nylon filters into clean vials. Antisolvent was then added to the sample solutions. Precipitates that formed were collected by vacuum filtration.

Slurries: Saturated solutions of Form A containing excess solid were prepared in various solvents. The samples were placed on a shaker block and agitated at a set temperature for a period of time. Solids were later collected for analysis by decanting the solutions or by vacuum filtration.

Vapor Diffusions (VD): Form A was dissolved in test solvents. These solutions were passed through a 0.2-μm filter into small vials. The small vials were placed, uncovered, into larger vials containing a miscible antisolvent. The large vials were capped, sealed with Parafilm® and kept at ambient conditions. Solids that formed were isolated and analyzed.

Vapor Stress (VS) Experiments: Form A was dispensed into a small vial, which was placed, uncapped, in a larger vial containing a diffusing solvent. The larger vial was sealed and stored at ambient temperature. Samples were also stressed in ovens at elevated temperatures and under different relative humidity conditions.

Capillary Evaporations (CE): Solutions of Form A were filled into glass capillaries by centrifugation. The capillary samples were then allowed to evaporate.

Crash Cools (CC): Samples of Form A in different solvents were prepared and passed through 0.2-μm nylon filters into clean vials. The vials containing solutions were then rapidly cooled by submersion in a dry ice/acetone bath for several seconds. Solids that precipitate were collected by filtration and dried.

Milling Experiments: A small amount of Form A was placed in a grinding holder with milling ball and the holder capped. The sample was then ground in a mixer miller at a frequency of 30 Hz for a measured time interval. The solids were examined using optical microscopy. Several samples were wet-milled by adding sufficient water to the sample to dampen it before milling.

Cryogrinding Experiments: A small amount of Form A was ground at a frequency of 10 Hz for a total of 6 minutes using a Spex Centriprep 6750 freezer miller filled with liquid nitrogen. The sample was allowed to cool for one minute after every two minute grinding cycle. The sample was removed from the mill and allowed to equilibrate to room temperature in a large desiccator.

Example 3

X-Ray Powder Diffraction

X-ray powder diffraction analyses were performed using a Shimadzu XRD-6000 X-ray powder diffractometer using Cu Kα radiation. The instrument is equipped with a long fine focus X-ray tube. The tube voltage and amperage were set to 40 kV and 40 mA, respectively. The divergence and scattering slits were set at 1° and the receiving slit was set at 0.15 mm. Diffracted radiation was detected by a NaI scintillation detector. A θ-2θ continuous scan at 3°/min (0.4 sec/0.02° step) from 2.5 to 40 °2θ was used. A silicon standard was analyzed to check the instrument alignment. Data were collected and analyzed using XRD-6000 v. 4.1. Samples were prepared for analysis by placing them in an aluminum holder with silicon insert.

X-ray powder diffraction (XRPD) analyses were also performed using an Inel XRG-3000 diffractometer equipped with a CPS (Curved Position Sensitive) detector with a $2\theta$ range of 120°. Real time data were collected using Cu-K$\alpha$ radiation starting at approximately 4 $°2\theta$ at a resolution of 0.03 $°2\theta$. The tube voltage and amperage were set to 40 kV and 30 mA, respectively. The monochromator slit was set at 5 mm by 80 µm. The pattern is displayed from 2.5-40 $°2\theta$. Samples were prepared for analysis by packing them into thin-walled glass capillaries. Each capillary was mounted onto a goniometer head that is motorized to permit spinning of the capillary during data acquisition. The samples were analyzed for 5 min. Instrument calibration was performed using a silicon reference standard.

Data Collection: A colorless plate of $C_{18}H_{22}N_5O_2, C_7H_5O_2$ having approximate dimensions of 0.50×0.35×0.28 mm was mounted on a glass fiber in a random orientation. Preliminary examination and data collection were performed Mo $K_\alpha$ radiation ($\alpha$=0.71073 Å) on a Nonius KappaCCD equipped with a graphite crystal, incident beam monochromator. Cell constants for data collection were obtained from least-squares refinement, using the setting angles of 13398 reflections in the range $2<\theta<27°$. The refined mosaicity from DENZO/SCALEPACK was 0.41° indicating good crystal quality. The space group was determined by the program XPREP. From the systematic presences of: h00 h=2n, 0k0 k=2n, 00l l=2n and from subsequent least-squares refinement, the space group was determined to be $P2_12_12_1$ (no. 19). The data were collected at a temperature of 423 K. Data were collected to a maximum $2\theta$ of 55.1°.

Data Reduction: A total of 13398 reflections were collected, of which 4589 were unique. Frames were integrated with DENZO-SMN. Lorentz and polarization corrections were applied to the data. The linear absorption coefficient is 0.9/cm for Mo $K_\alpha$ radiation. An empirical absorption correction using SCALEPACK was applied. Transmission coefficients ranged from 0.943 to 0.976. A secondary extinction correction was applied. Intensities of equivalent reflections were averaged. The agreement factor for the averaging was 10.2% based on intensity.

Structure Solution and Refinement: The structure was solved by direct methods using SIR2002. The remaining atoms were located in succeeding difference Fourier syntheses. Hydrogen atoms were included in the refinement but restrained to ride on the atom to which they are bonded. The structure was refined in full-matrix least-squares by minimizing the function:

$$\Sigma w(|F_o|^2 31 |F_c|^2)^2$$

The weight w is defined as $1/[\sigma^2(F_o^2)+(0.1225P)2]$ where $P=(F_o^2+2F_c^2)/3$.

Scattering factors were taken from the "International Tables for Crystallography". Of the 4589 reflections were used in the refinements, only the 2414 reflections with $F_o^2>2\sigma(F_o^2)$ were used in, calculating R. The final cycle of refinement included 321 variable parameters and converged (largest parameter shift was <0.01 times its estimated standard deviation) with unweighted and weighted agreement factors of:

$$R = \sum |F_o - F_c| / \sum F_o = 0.068$$

$$R_w = \sqrt{(\sum w(F_o^2 - F_c^2)^2 / \sum w(F_o^2)^2)} = 0.150$$

The standard deviation of an observation of unit weight was 1.06. The highest peak in the final difference Fourier had a height of 0.34 e/A$^3$. The minimum negative peak had a height of –0.45 e/A$^3$. The factor for the determination of the absolute structure refined to –1.00. Refinement was performed on a LINUX PC using SHELX-97. Crystallographic drawings were done using programs ORTEP.

Computation of Disorder and Amorphous Content of Milled Samples: The weight percent crystallinity of milled samples was determined by calculation using two software packages. Shimadzu percent crystallinity module, which is part of the Shimadzu XRD-6000 software package, was used for samples with significant amorphous content. In-house software was used for largely crystalline samples, as the Shimadzu software was less accurate at low amorphous concentrations. For the in-house software, X-ray powder data was first smoothed and then a series of digital filters is applied to separate the data into three components: crystalline, amorphous and disordered. A background correction was also applied. The percent amorphous content was then calculated by determining the ratio of amorphous to the sum total of all three components. Both methods were run under non-GMP conditions and provide approximate values only.

Milling Studies: Dry milling Form A at ambient and liquid nitrogen temperatures generated disordered Form A. Peak broadening, an offset baseline and reduced signal intensity were characteristic of the XRPD patterns of dry milled samples. Wet milling Form A and amorphous material with water produced crystalline Form A solids. Four milled samples were analyzed by XRPD. All patterns matched Form A, without visible amorphous content.

Calculation of Amorphous Content of a Milled Sample: XRPD patterns of milled samples of Compound I Forma A exhibited peak broadening as well as an amorphous halo. This suggested that two processes were contributing to the loss of crystallinity: crystallite size reduction causing the peak broadening and amorphous formation causing the offset baseline. A dry milled sample 1966-04-02 (milled for 30 minutes) was chosen for the study and the XRPD pattern of Form A (lot no. QZ-656-17(1)) used as a reference standard of Form A. The weight percent of amorphous material of the dry milled sample 1966-04-02 was estimated to be around 58% by calculation. Lot 635-181-1 contained around 13% amorphous content by weight. Values determined by computation are approximate, particularly at low amorphous content.

Example 4

Differential Scanning Calorimetry (DSC)

Differential scanning calorimetry was performed using a TA Instruments differential scanning calorimeter 2920. The sample was placed into an aluminum DSC pan, and the weight accurately recorded. The pan was covered with a lid and then crimped. The sample cell was equilibrated at ambient temperature and heated under a nitrogen purge at a rate of 10° C./min, up to a final temperature of 350° C. Indium metal was used as the calibration standard. Reported temperatures are at the transition maxima.

For studies of the glass transition temperature (Tg) of the amorphous material, the sample cell was equilibrated at room temperature, then heated under nitrogen at a rate of 10°

C./min, up to 100° C. The sample cell was then cooled to −40° C. before being heated again at a rate of 10° C./min up to a final temperature of 350° C. The $T_g$ is reported from the inflection point of the transition.

Cyclic DSC experiments were carried out by placing accurately weighed samples in uncrimped pans. Samples were heated under nitrogen at a rate of 10° C./min to either 150 or 180° C. subsequently cooled to −40° C. This procedure was repeated twice before the sample was heated to 250° C.

Example 5

Thermogravimetric Analysis (TGA)

Thermogravimetric analyses were performed using a TA Instruments 2950 thermogravimetric analyzer. Each sample was placed in an aluminum sample pan and inserted into the TG furnace. The furnace was first equilibrated at ambient temperature, then heated under nitrogen at a rate of 10° C./min, up to a final temperature of 350° C. Nickel and Alumel™ were used as the calibration standards.

Example 6

Hot Stage Microscopy (HSM)

Hot stage microscopy was performed using a Linkam hot stage mounted on a Leica DM LP microscope. Samples were observed using a 20× objective with a lambda plate with crossed polarizers. Samples were sandwiched between two coverslips and visually observed as the stage was heated. Images were captured using a SPOT Insight™ color digital camera with SPOT Software v. 3.5.8. The hot stage was calibrated using sulfapyridine and vanillin USP melting point standards.

Example 7

Fourier Transform Infrared Spectroscopy (FT-IR)

Infrared spectra were acquired on a Magna-IR 860® Fourier transform infrared (FT-IR) spectrophotometer (Thermo Nicolet) equipped with an Ever-Glo mid/far IR source, a potassium bromide (KBr) beamsplitter, and a deuterated triglycine sulfate (DTGS) detector. An ATR Thunderdome accessory with non-concave tip was used for sampling. Sample preparation consisted of placing the sample on a germanium crystal and pressing the material against the crystal using a plunger. Each spectrum represents 256 co-added scans collected at a spectral resolution of 4 $cm^{-1}$. An air background data set was acquired. A Log 1/R (R=reflectance) spectrum was acquired by taking a ratio of these two data sets against each other. Wavelength calibration was performed using polystyrene.

Infrared spectra were also acquired using a diffuse reflectance accessory (the Collector™, Thermo Spectra-Tech). Sample preparation consisted of placing the sample into a 13-mm diameter cup. A background data set was acquired with an alignment mirror in place. A Log 1/R (R=reflectance) spectrum was acquired by taking a ratio of these two data sets against each other. Wavelength calibration was performed using polystyrene.

Example 8

Raman Spectroscopy

FT-Raman spectra were acquired on an FT-Raman 960 spectrometer (Thermo Nicolet). This spectrometer uses an excitation wavelength of 1064 nm. Approximately 0.6-0.8 W of Nd:YVO$_4$ laser power was used to irradiate the samples. The Raman spectra were measured with an indium gallium arsenide (InGaAs) detector. The samples were prepared for analysis by placing the material in a glass capillary or NMR tube. A total of 256 sample scans were collected from 400-3600 $cm^{-1}$ at a spectral resolution of 4 $cm^{-1}$, using Happ-Genzel apodization. Wavelength calibration was performed using sulfur and cyclohexane.

Example 9

NMR Spectroscopy

Solution $^1$H NMR spectra can be acquired at ambient temperature on a Bruker Instruments AM-250 spectrometer at a magnetic field strength of 5.87 Tesla ($^1$H Larmor frequency=250 MHz). The samples can be dissolved in NMR-grade DMSO-d$_6$. Spectra can be acquired with a $^1$H pulse width of 8.5 μs (90°), a 2.5 second acquisition time, a 5.0 second delay between scans, a spectral width of 6400.0 Hz with 32K data points, and 32 co-added scans. Each free induction decay (FID) can be processed with GRAMS/32 AI software v. 6.00 using a Fourier number equal to twice the number of acquired points [or a larger multiple if zero filling is used] with an exponential line broadening factor of 0.2 Hz to improve sensitivity. Peak tables can be generated by the GRAMS software peak picking algorithm. For these spectra the residual peak from incompletely deuterated DMSO-d$_6$ is located at approximately 2.50 ppm.

Example 10

Moisture Sorption/Desorption Analyses

Moisture sorption/desorption data were collected on a VTI SGA-100 Vapor Sorption Analyzer. Sorption and desorption data were collected over a range of 5% to 95% relative humidity (RH) at 10% RH intervals under a nitrogen purge. Samples were not dried prior to analysis. Equilibrium criteria used for analysis were less than 0.0100% weight change in 5 minutes, with a maximum equilibration time of 3 hours if the weight criterion was not met. Data were not corrected for the initial moisture content of the samples. NaCl and PVP were used as calibration standards.

Example 11

Karl Fischer Water Analysis

Karl Fischer (titrimetric) water analysis can be performed according to U.S. Pharmacopoeia, vol. 24, method 921, U.S.P. Pharmacopeial Convention, Inc, Rockville, Md. The polymorph can be tested for water content by Karl Fischer titration using a coulometer according to the published procedure and the manufacturer's coulometer instructions.

While the present invention is disclosed with reference to certain embodiments and examples detailed above, it is to be understood that these embodiments and examples are intended to be illustrative rather than limiting. As such, it is contemplated that various modifications and variations will be apparent to those skilled in the art and intended that those modifications and variations fall within the scope of the invention and the appended claims. All patents, patent applications, papers, and books cited in this application are incorporated by reference herein in their entirety.

What is claimed is:

1. A method for preparing Compound I having the formula

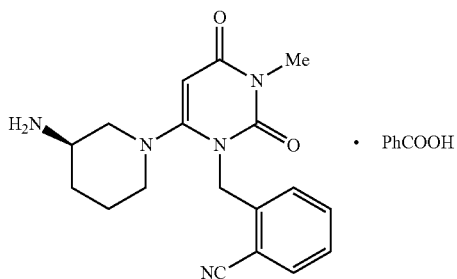 · PhCOOH wherein Compound I is greater than 90% by weight polymorph Form A characterized by
an X-ray powder diffraction pattern with salient features being major diffraction lines as follows:

| Position (°2θ) | 9.44 | 10.84 | 17.82 | 18.75 | 25.87 | 28.52 |
| --- | --- | --- | --- | --- | --- | --- | using Cu-Kα radiation;

the method comprising:
(a) crystallization from any of the following solvent systems consisting of (i) acetone, (ii) acetonitrile; (iii) butanol, (iv) dimethylsulfoxide; (v) dioxane; (vi) ethanol; (vii) ethanol and isopropyl alcohol; (viii) ethanol and water; (ix) ethyl acetate; (x) heptane; (xi) isopropanol; (xii) isopropyl acetate; (xiii) methyl ethyl ketone; (xiv) methyl isobutyl ketone; (xv) 2,2,2-trifluoroethanol; (xvi) tetrahydrofuran; (xvii) toluene; (xviii) water; and (xix) ethanol and heptane; or
(b) by the conversion of an amorphous Form 1 of Compound I by heating the amorphous Form 1 of Compound I at a temperature of >40° C., by subjecting the amorphous Form 1 of Compound I to relative humidity of between about 85% and 95% or organic vapors selected from the group consisting of ethyl acetate, isopropyl alcohol and tetrafluoroethylene, or by wet milling of amorphous Form 1 of Compound I with water.

\* \* \* \* \*